(12) United States Patent
Alghorani et al.

(10) Patent No.: US 12,733,878 B2
(45) Date of Patent: Sep. 15, 2026

(54) SYSTEM AND METHODS FOR COLLECTING AND PROCESSING DATA ON ONE OR MORE PHYSIOLOGICAL PARAMETERS OF MONITORED SUBJECT

(71) Applicant: LAKEHEAD UNIVERSITY, Thunder Bay (CA)

(72) Inventors: Yahia Ghazi Husni Alghorani, Amman (JO); Salama Ikki, Thunder Bay (CA)

(73) Assignee: Lakehead University, Ontario (CA)

( * ) Notice: Subject to any disclaimer, the term of this patent is extended or adjusted under 35 U.S.C. 154(b) by 546 days.

(21) Appl. No.: 17/695,311

(22) Filed: Mar. 15, 2022

(65) Prior Publication Data

US 2022/0296169 A1 Sep. 22, 2022

Related U.S. Application Data

(60) Provisional application No. 63/162,072, filed on Mar. 17, 2021.

(51) Int. Cl.
*A61B 5/00* (2006.01)
*A61B 5/0205* (2006.01)
(Continued)

(52) U.S. Cl.
CPC ............ *A61B 5/721* (2013.01); *A61B 5/0024* (2013.01); *A61B 5/02055* (2013.01);
(Continued)

(58) Field of Classification Search
None
See application file for complete search history.

(56) References Cited

U.S. PATENT DOCUMENTS 4,960,126 A * 10/1990 Conlon ................ A61B 5/7285 600/513
9,913,575 B2 * 3/2018 Gazdzinski .......... A61B 5/6861
(Continued)

FOREIGN PATENT DOCUMENTS

WO WO-2010077997 A2 * 7/2010 .......... A61B 5/0022

*Primary Examiner* — Benjamin J Klein
*Assistant Examiner* — Willow Grace Welch
(74) *Attorney, Agent, or Firm* — Kyle R Satterthwaite; Ryan W Dupuis; Ade & Company Inc

(57) ABSTRACT

A method of collecting physiological parameter data of a monitored subject comprises measuring a biosignal from which the physiological parameter is deducible, including noise; converting the noisy measured biosignal to a vector having different frequency components with corresponding magnitude coefficients; discarding select frequency components with coefficients below a prescribed threshold; and communicating the reduced vector to a computing device for processing to deduce the physiological parameter. A method of processing physiological parameter data comprises receiving a measured biosignal with electromagnetic interference noise; obtaining from the noisy measured biosignal representative data using a machine learning algorithm; and determining the physiological parameter from the representative data. A system for monitoring a physiological parameter comprises a wearable sensor configured to measure a biosignal and to remove noise from the measured signal, and a portable computing device configured to receive a transmitted signal from the sensor and to determine the physiological parameter therefrom.

20 Claims, 8 Drawing Sheets

(51) Int. Cl.
*A61B 5/024* (2006.01)
*A61B 5/026* (2006.01)
*G16H 40/67* (2018.01)
*G16H 50/20* (2018.01)

(52) U.S. Cl.
CPC .......... *A61B 5/7232* (2013.01); *A61B 5/7267* (2013.01); *A61B 5/7278* (2013.01); *G16H 40/67* (2018.01); *G16H 50/20* (2018.01); *A61B 5/02438* (2013.01); *A61B 5/026* (2013.01)

(56) References Cited

U.S. PATENT DOCUMENTS

| | | | | |
|---|---|---|---|---|
| 2013/0231947 | A1* | 9/2013 | Shusterman | G16H 40/67<br>705/2 |
| 2014/0107457 | A1* | 4/2014 | Raghunathan | A61B 5/7203<br>600/509 |
| 2014/0180039 | A1* | 6/2014 | LeBoeuf | A61B 5/165<br>600/324 |
| 2014/0200423 | A1* | 7/2014 | Eisen | A61B 5/7278<br>600/340 |
| 2015/0112220 | A1* | 4/2015 | Sana | A61B 5/05<br>600/534 |
| 2015/0220486 | A1* | 8/2015 | Karakonstantis | G06F 17/142<br>708/405 |
| 2017/0340292 | A1* | 11/2017 | Rossi | A61B 5/7267 |
| 2019/0105011 | A1* | 4/2019 | Kim | G06F 18/295 |
| 2021/0052227 | A1* | 2/2021 | Engman | A61B 5/7217 |
| 2021/0059540 | A1* | 3/2021 | Peterson | A61B 5/7267 |
| 2021/0166577 | A1* | 6/2021 | Hong | A61B 5/6803 |

* cited by examiner

SYSTEM AND METHODS FOR COLLECTING AND PROCESSING DATA ON ONE OR MORE PHYSIOLOGICAL PARAMETERS OF MONITORED SUBJECT

This application claims the benefit under 35 U.S.C. 119(e) of U.S. provisional application Ser. No. 63/162,072 filed Mar. 17, 2021 which is incorporated by reference herein.

FIELD OF THE INVENTION

The present invention relates generally to a system and methods for collecting and processing data on one or more physiological parameters of a monitored subject, and more particularly to such a system and methods implementable using widely commercially available wearable and handheld portable computing devices, such as smartwatches, smart-patches and smartphones.

BACKGROUND

The COVID-19 pandemic greatly highlighted the need to harness our vital digital technology and use it to monitor patients remotely. The rapidly increasing numbers of patients and the long duration of hospitalization place great strain on the current healthcare system. By following social distancing recommendations, continuous monitoring of patients (including those with chronic diseases) at home is critical to preventing rapid deterioration. When used with predictive platforms, wearable biosensor users can be alerted when changes in physiological parameters match those associated with COVID-19.

Physiological parameters (e.g., skin temperature, oxygen saturation (SpO2), blood pressure (BP), heart rate (HR), and respiration rate (RR)) are used to assess a COVID-19 patient's health. With some exceptions, for example in intensive care units (ICUs), measurements of the parameters are not made continuously in a healthcare facility or at home. This has consequences: sudden changes indicating a rapid deterioration of the patient's health may not be detected in time. This is particularly relevant to the epidemic of COVID-19 as rapidly increasing numbers of patients and long hospitalization periods place a significant workload on the healthcare system. While some patients need hospitalization, most do not. To monitor those at home, accurate data is vital. There are several reasons that prevent this monitoring process; most involve cost. The service life of most monitors is quite long, which means that many of them were developed when the practice was to measure one parameter and register by hand. Replacing such units will be very expensive unless a low-cost solution is developed. Adapting these units instead of replacing them, as well as being expensive, would severely restrict the movement and behavior of a mobile patient, resulting in skewed measurements. For BP, the obtrusive nature of commonly available monitors can actually affect the measurement (i.e., cuff inflation hypertension). High BP (hypertension) is a critical factor for increasing the risk of developing serious diseases, including cardiovascular diseases such as stroke and heart failure, as well as kidney disease. Thus, BP is an important physiological parameter that must be monitored regularly for early detection. For this challenge, the preferred artery to be utilized for BP measurement is the carotid. Currently, the only way to measure non-invasive carotid BP that can be deployed at home is applanation tonometry (AT). AT is used clinically outside North America for clinical research purposes. However, AT requires fully trained, experienced operators and compatible patients. So, an alternative to AT to determine carotid BP is highly desirable. For RR, only a few wearable biosensors are able to measure RR continuously compared to other major physiological parameters, such as skin temperature, HR, and SpO2. Many of them use impedance plethysmography and inductance plethysmography sensors. This requires putting a narrow band around the chest of the wearer, which is uncomfortable when wearing it for long periods. Impedance pneumography is the most used RR sensor in hospitals and is not commonly integrated into wearable biosensors; therefore, it is also desirable to find an alternative solution for RR estimation.

To be truly effective during the COVID-19 pandemic, wearable biosensors must be widely available and therefore low cost. Advances in materials and microelectronics have led to devices capable of unobtrusively measuring the five physiological parameters [1]. While individually impressive, an integrated, low-cost solution has yet to be developed that would allow patients to return home and resume their normal lives while still being monitored. Managing and monitoring of physiological parameters requires efficient wearable sensing platforms (e.g., wristwatch, vital patch) that can capture physiological signals/biometrics (e.g., skin temperature, electrocardiogram (ECG), photoplethysmography (PPG)) in real-time, and deliver data from the patient to IoT edge computing devices (e.g., smartphones, tablets) to detect the physiological parameters, to be transferred to the cloud for medical analysis (see, e.g., FIG. 1). The IoT edge computing architecture consists of a large number of real-time edge devices that collect large amounts of data from patients in different locations and make them accessible to clinicians at any time for analysis. By exchanging medical records for patients between public and private hospitals, doctors and specialists would be able to predict where the COVID-19 patient is located on the spectrum of disease progression more accurately and efficiently.

The field of artificial intelligence (AI) and machine learning offers several powerful tools to improve and optimize most traditional patient monitoring processes [2]. Applying AI in healthcare is a compelling vision that can lead to significant improvements in real-time monitoring at lower costs. When combined with remote monitoring and machine learning, we get better diagnoses with less specialized work, so that we can reduce costs and diagnose diseases faster and more accurately. Machine learning techniques can be used to calibrate low-cost biosensors on the field based on influencing environmental factors including motion artifacts and interference. Sensor calibration is defined as checking and adjusting the sensor's response to ensure accurate measurements are reported. IoT sensor manufacturers often calibrate wearable biosensors before they are launched on the market, however, sensor calibration is usually done in controlled laboratory conditions that do not represent the exact conditions (e.g., body motion including mobilization after surgery and exercise [3], inter and intra-sensor interference [4], [5]) that the wearable biosensors encounter when deployed to the field. Therefore, wearable biosensors may still report inaccurate values (due to the low signal-to-noise ratio values) in the field even after they have been calibrated in the laboratory. Developing machine learning-based calibration models can help improve data quality and ensure that low-cost biosensors collect accurate data. However, achieving low-cost biosensor calibration requires 1) identifying the factors that affect the quality of sensor data for a given measurement, 2) modeling the effects of these factors on the sensor's response, and 3) selecting the machine learning algorithm to correct sensor output errors and improve data visualization.

Extracting a training set of features/attributes from wearable biosensors (e.g., skin temperature, ECG, PPG sensors) can be relatively small, resulting in poor detection and classification. Training a sensor calibration model (e.g., neural network classifier) with a limited set of data points can cause the model (classifier) to memorize all examples of training, resulting in a problem of overfitting and poor performance on unseen data. In practice, the main challenge is to implement remote monitoring of physiological parameters in sensor fault scenarios due to some mechanical defects, motion artifacts, or high noise interference (e.g., some of the selected feature values are incorrect because of errors in the data acquisition process or the pre-processing phase), resulting in lower detection accuracy. That is to say, more training data provides a richer description of the sensor fault problem that the classifier might learn from to prevent overfitting.

The effect of motion (including respiratory and cardiac motion) on the sensor's physiological parameters is well known. It differs depending on the sensing method (e.g., the electrical methods are generally less vulnerable than the optical ones) and the motion's intensity and duration, which in turn limits the performance of classifiers, resulting in high detection errors. The mutual interference between wearable biosensors, e.g., intra-sensor interference due to the overlapping of biosignals transmission, can also reduce the received signal strength, which may result in significant degradation of signal detection. Besides intra-sensor interference, the incoming data traffic may interfere with other data traffics caused by nearby IoT devices (e.g., inter-sensor interference generated by RF radiation) operating in the 2.4 GHz unlicensed ISM radio bands [5], resulting in a high noise level in biosignals (i.e., low data quality and accuracy). From a physical layer perspective, the presence of noise and interference in the biosignals requires an increase the number of measurements/samples needed by the calibration model to improve the quality of the reconstructed biosignals, making the resolution of the sampling devices, such as digital-to-analog converters (DACs) and analog-to-digital converters (ADCs), high, i.e., high-cost hardware implementation and power consumption of patient monitoring systems. With a complete set of discrete-time samples of a biosignal, the design of high-speed sampling devices becomes more complicated for BLE-enabled wearable biosensors and edge devices, leading to large energy consumption due to continuous monitoring of biosignals.

Several studies have been conducted in the area of smart healthcare environments and showed significant benefits. For instance, Kachuee et al. [7] proposed a cuff-less blood pressure estimation algorithm based on the pulse arrival time (PAT) extracted from the ECG and PPG signals. The proposed algorithm implemented a denoising method such as discrete wavelet transformation (DWT) to remove noise and artifacts from the ECG and PPG signals, and used various machine learning techniques (such as linear regression, decision tree, support vector machine, random forest) to achieve an accurate and continuous BP estimate. DWT provides high data compression with low signal loss; yet, it is highly computational, memory-intensive, and energy-consuming compared to CS [8]. Although the proposed algorithm worked well without calibration, a calibration procedure was suggested to increase the estimation accuracy. Tanveer and Hasan [9] proposed a waveform-based hierarchical artificial neural network—long short-term memory (ANN-LSTM) model for continuous BP estimation. It was found that the proposed model is able to automatically extract the necessary features (e.g., pulse transit time (PTT) values, pulse wave velocity (PWV), heart rate, and systolic upstroke time (ST), diastolic time (DT)) from the PPG and ECG waveforms, providing an accurate prediction for long-term BP measurements compared to classical models.

Ripoll and Vellido [10] introduced a non-invasive algorithm for estimating BP, in which PTT was measured using PPG and ECG signals. The study relies on the restricted Boltzmann machine (RBM)-ANN model to remove motion artifacts and noisy segments from the dataset. The accuracy received grades A and B according to British hypertension society (BHS). The main limitations of this method are: the accuracy of the model decreases after 6 minutes from the initial calibration, and the model is unable to estimate long-term continuous BP because it suffers from a vanishing and exploding gradient problem during training [2]. Lazazzera et al. [11], developed a new smartwatch to estimate BP from PPG signals using PTT and HR. Two PPG signals were recorded to filter motion artifacts: one from the index finger and one from the wrist, while the BP reference signal was measured by a sphygmomanometer. The experimental results showed that the estimation accuracy was improved using regression analysis and it almost agreed with the association for the advancement of medical instrumentation (AAMI) criteria. The main drawback of this method is the use of two PPG sensors to monitor BP, where the user has to place a finger from the other hand on an electrode to record the PPG signal, which is an impractical solution, especially if continuous BP measurement is required. Although the PPG technology used in estimating BP has not yet matured, it is expected that in the near future, accurate and continuous measurements of BP may be available from smartphones and wearables due to its enormous potential [12].

PPG and ECG technology represents a convenient and low-cost solution that can be applied to measure multiple physiological parameters including HR, RR and SpO2. For example, Pimentel et al [13] developed a probabilistic approach that uses Gaussian process regression to measure RR from different sources of modulation in PPG signals such as baseline wander (BW), amplitude modulation (AM), and frequency modulation (FM). In this study, the signal quality is assessed using the correlation between the extracted signal and the true reference signal. Charlton et al [14] estimated RR by analyzing ECG and PPG features (e.g., BW, AM, FM), as the extracted signal quality was assessed by calculating the correlation with the true reference signal using the Pearson's correlation coefficient. The results showed that ECG provides higher quality RR than PPG. Motin et al. [15] proposed an algorithm that uses the ensemble empirical mode decomposition method with principal component analysis (PCA) to extract HR and RR from PPG signals. The proposed algorithm was more accurate in estimating RR and HR than other existing methods. While ECG-based respiration extract is a validated approach [16], [17], and can be more precise than PPG [18], its adoption is limited by access to an appropriate continuous ECG monitor. Ravichandran et al. [19] proposed a DL model to extract RR from PPG. The accuracy was found to be better than that obtained from conventional approaches. However, extensive training on a wide range of breathing anomalies must be performed under patient movement conditions and the corresponding performance study should be evaluated.

Wrist-based PPG sensors are becoming popular across the healthcare system that can be used to measure pulse oximetry (i.e., for continuous non-invasive monitoring of HR and SpO2) because of their wearable implementation compared to conventional finger-based PPG sensors and chest-based ECG sensors [20]. The PPG approach is generally simple, inexpensive and convenient and can be easily integrated into wristwatches. Lee et al. [3] developed a motion artifact reduction algorithm based on independent component analysis (ICA) to measure HR from PPG signals. The ECG system used as a reference for the HR is attached to the vital patch to detect R-R intervals (RRI), while the multi-channel PPG measurement system is worn on the wrist to detect peak-to-peak intervals (PPI) [21]. The evaluation showed that the proposed method is effective in reducing errors in estimating HR in situations of intense movement such as fast walking and running. PPG-based HR monitors provide a popular alternative to ECG as they can be placed in various locations of the body such as earlobes, fingertips, or wrist, making them suitable for daily, mobile use [22].

Kiruthiga, et al. [23] studied the reflectance PPG for SpO2 monitoring from different measurement locations on the body (such as finger, wrist, chest, and forehead) where the main feature is extracted from the AC (pulsatile) and DC (non-pulsatile) components of the red and near infrared (NIR) PPG signals. The results showed that the linear regression model for wrist reflectance PPG has a lower correlation coefficient (i.e., accuracy) than that for finger reflectance PPG due to motion artifacts. Modern wearable devices on the wrist, such as Apple Watch, FitBit, and Samsung Gear, have a built-in sensor called a pulse oximeter. While pulse oximeters are able to measure both SpO2 and HR, current wrist-worn devices use them only to estimate HR as SpO2 measurements are inaccurate in the presence of motion artifacts [20], [24]. However, most of the ECG-PPG wearables (e.g., smartwatch) on the market at the moment are complex and expensive that do not provide continuous monitoring of the physiological parameters (including BP) and require the user to place a finger from the other hand on an electrode for a period of time (e.g., 30 to 45 seconds [25], [26]) to monitor HR, RR, SpO2, and BP, which is an ineffective solution especially if continuous monitoring is required during patient movement (see, e.g., [27-34]). In addition, the current e-health monitoring systems available in the market today (e.g., VivaLnk, MedTach, Cloud DX, VitalConnect, Spire Health, QardioMD) are costly and lack continuous BP monitoring while the patient is in motion. This is because they use cuff-based BP-monitoring devices that require the patient to be at rest (i.e., a lot of time and effort) to do the monitoring, which is inconvenient and makes continuous monitoring impossible. Although their chest-based ECG solutions are FDA/CE certified, they are expensive and lack continuous BP monitoring feature.

Although previous studies have enhanced the detection and monitoring of physiological parameters across wearables, the proposed methods were of a high degree of computational complexity (i.e., high-cost, high-power devices) and redundant/noisy features due to motion artifacts and increased computational requirements for the sampling devices used to restore the PPG-ECG signals. In reality, redundant or noisy features can damage the accuracy of the sensor calibration models, resulting in less accurate predictions. Therefore, pre/post-processing techniques must be adopted to reduce the cost and power consumption of physiological data monitoring devices and improve the detection accuracy of PPG-ECG signals. However, few studies have found that the CS technique can be applied to reduce the motion artifacts in PPG-ECG recordings and the sampling rates required to extract the physiological parameters (see, e.g., [35-40]). To realize ultra-low power wearable biosensors, we developed a low-complexity algorithm [41], based on CS and ICA that can reduce and eliminate artifacts and interference in sparse biosignals. The proposed method supports real-time patient monitoring systems that improves the detection of source biosignals (e.g., ECG). Our results and analysis indicated that the CS-ICA algorithm helps to develop low-cost, low-power wearable biosensors while improving data quality and accuracy for a given measurement. By implementing the sensing method, the error in reconstructing biosignals is reduced, and the sampling devices operate at low-speed and low-resolution.

SUMMARY OF THE INVENTION

It is an object of the to develop an energy-efficient sensor calibration model based on deep learning (DL) that can improve the classification accuracy of ECG and PPG patterns and eliminate motion artifacts and interference in sensor readings. While DL is very effective in classifying ECG and PPG signals during noisy measurement, it is an energy-consuming model since it uses multiple layers to gradually extract high-level features from the raw data input. To develop low-cost, low-power calibration model, we employ compressed sensing (CS) techniques to classify the PPG-ECG signals through a few multiple layers, i.e., low computation time, where the physiological parameters are retrieved in only a few measurements. Using the joint CS-DL recovery, we can employ low-speed and low-resolution DACs (i.e., sub-Nyquist sampling rates and low bit-depths) to detect and estimate the physiological parameters.

It is an object of the invention to design a low-cost sensor system that allows continuous remote monitoring of physiological parameters for COVID-19 patients in real-time, which employs machine learning and compressed sensing to improve the classification accuracy of PPG and ECG signals and reduce training time, power consumption, and computing costs for BLE-enabled wearable and edge computing devices. Specifically, the aim is to design and develop an accurate multi-parameter calibration model (based on deep learning, compressed sensing, and multi-linear regression) that can i) provide accurate detection and classification of ECG and PPG patterns during patient movement (where biosignals are most susceptible to motion artifacts and RF interference), ii) estimate the five physiological parameters (e.g., skin temperature, BP, RR, HR, SpO2) continuously at a low-cost that in line with AAMI/medical-grade sensors (FDA/Health Canada).

establish a prototype for the sensor calibration model using wearable development platforms (such as health sensor platforms-Maxim that can be used as a vital patch and can be worn on the wrist) and to implement the calibration model on an edge device that can estimate the physiological parameters and reduce the computational complexity and power consumption of sampling devices.

According to an aspect of the invention there is provided a method of collecting data on a physiological parameter of a monitored subject for processing, the method comprising:

measuring a biosignal, from which the physiological parameter is deducible, to form a signal comprising data representative of the physiological parameter and noise data;

converting the signal to a vector having a plurality of different frequency components each with a corresponding magnitude coefficient;

discarding from the vector select ones of the frequency components with coefficients below a prescribed threshold to form a reduced vector; and communicating the reduced vector to a computing device for processing to deduce the physiological parameter.

This arrangement accounts for noise inadvertently captured during measurement of the biosignal and provides reduced computational burden for the computing device by removing components from the measured signal which are immaterial to the physiological parameter, such that the computing device receives a smaller amount of transmitted data.

Typically, the biosignals used are electrical biosignals.

In one arrangement, the step of measuring a biosignal is performed using a wearable sensor configured for attaching to the monitored subject, typically a human, and the step of communicating the reduced vector is performed wirelessly to the computing device which is operatively communicated with the wearable sensor.

Preferably, when measuring the biosignal is performed using a wearable sensor, the noise data comprises noise associated with movement of the wearable sensor.

In one arrangement, the prescribed threshold is based on noise associated with movement of a wearable sensor.

Preferably, the method further includes measuring motion of the monitored subject to form motion data usable to remove the noise data from the measured biosignal.

In one arrangement, converting the signal to a vector comprises performing an inverse discrete cosine transform on the signal and quantizing the transformed signal.

Preferably, discarding from the vector select ones of the frequency components with coefficients below a prescribed threshold to form a reduced vector comprises digitally compressing the vector.

According to another aspect of the invention there is provided a method of processing data collected on a physiological parameter of a monitored subject, the method comprising:

receiving a noisy signal of a measured biosignal, wherein the noisy signal comprises data representative of the physiological parameter and noise data;

obtaining from the noisy signal the data representative of the physiological parameter using a machine learning algorithm, wherein the noise data comprises noise associated with electromagnetic interference; and determining the physiological parameter from the data obtained by the machine learning algorithm.

This provides an arrangement with generally low computation burden to enable continuous monitoring of Typically, the step of receiving the noisy signal is performed using a computing device, and the noisy signal is wirelessly transmitted thereto from a remote sensor performing measurement of the biosignal.

Typically, the noisy signal is in the form of a vector having a plurality of different frequency components each with a corresponding magnitude coefficient.

Typically, the steps of (i) obtaining from the noisy signal the data representative of the physiological parameter using a machine learning algorithm, and (ii) determining the physiological parameter from the data obtained by the machine learning algorithm, are performed using a portable computing device, such as a smartphone or a tablet computer, which has an electrical battery as a power source.

Preferably, the machine learning algorithm comprises an artificial neural network.

Preferably, the machine learning algorithm comprises a pattern recognition learning model.

Preferably, the pattern recognition learning model comprises a cost function configured to adjust weights and biases of the artificial neural network using gradient descent and backpropagation.

Preferably, the pattern recognition learning model comprises an activation function configured to average weights of the artificial neural network over a plurality of observations.

Preferably, the pattern recognition learning model is configured to determine a relationship between the physiological parameter and features extracted by the machine learning algorithm from the noisy signal using multiple linear regression.

Preferably, when the noisy signal is received from a plurality of sensors configured to measure the biosignal, the noise data additionally comprises overlapping data from the plurality of sensors, and the machine learning algorithm is configured to substantially remove said noise data. In other words, the noisy signal comprises a plurality of signals concurrently received from multiple sensors.

Preferably, when the noisy signal is received from a wearable sensor, the noise data additionally comprises noise associated with movement of the wearable sensor, and the machine learning algorithm is configured to substantially remove said noise data.

Preferably, when the noisy signal is received from a wireless sensor, the noise data additionally comprises ambient noise, and the machine learning algorithm is configured to substantially remove said noise data.

Preferably, determining the physiological parameter from the data representative thereof, which is obtained by the machine learning algorithm, comprises constructing a time-signal of the physiological parameter based on said data.

According to another aspect of the invention there is provided a system for monitoring a physiological parameter of a monitored subject comprising:

a wearable sensor configured for attaching to the monitored subject and configured to measure a biosignal, from which the physiological parameter is deducible, so as to form a measured signal including data representative of the physiological parameter and noise data;

wherein the wearable sensor comprises a non-transitory memory and a processor configured to execute instructions stored on the non-transitory memory to substantially remove, from the measured signal, the noise data so as to form a cleaned signal;

a portable computing device operatively communicated with the wearable sensor to receive a transmitted signal therefrom, wherein the portable computing device comprises a non-transitory memory and a processor configured to execute instructions stored on the non-transitory memory of the portable computing device to determine the physiological parameter from the transmitted signal.

This provides a sensor system using non-specialized commercially available computing devices which are relatively low-cost and widely available.

Preferably, the instructions stored on the non-transitory memory of the portable computing device to determine the physiological parameter from the transmitted signal comprise a machine learning algorithm.

Preferably, the machine learning algorithm is configured to substantially remove from the transmitted signal noise data associated with electromagnetic interference to isolate the cleaned signal therefrom.

Preferably, the machine learning algorithm is configured to substantially remove from the transmitted signal noise data associated with motion of the wearable sensor to isolate the cleaned signal therefrom.

Preferably, the system further includes a wearable sensor configured for attaching to the monitored subject and configured to measure motion of the monitored subject to form motion data to train the machine learning algorithm for removing the noise data associated with motion of the wearable sensor.

Preferably, the wearable sensor comprises a plurality of wearable sensors each measuring a different biosignal of the monitored subject from which a common physiological parameter is deducible.

BRIEF DESCRIPTION OF THE DRAWINGS

The invention will now be described in conjunction with the accompanying drawings in which.

In the drawings like characters of reference indicate corresponding parts in the different figures.

DETAILED DESCRIPTION

Referring to the accompanying figures, there are disclosed a method of collecting data on a physiological parameter of a monitored subject for processing, a method of processing the collected data, and a system for monitoring the physiological parameter.

The sensing approach adopted in this invention involves identifying the environmental factors that affect wearable biosensor outputs and that lead to poor detection of physiological parameters of COVID-19 patients. Unlike the machine learning models described in the literature, we develop an efficient sensor calibration model to improve detection of the physiological parameters and eliminate motion artifacts/noise interference in PPG-ECG sensor readings. The unique aspect of our approach will be to explicitly incorporate deep learning, compressed sensing, and multi-linear regression that offer significant energy savings for edge computing devices, addressing the sensor fault problem at an early stage and continually monitoring the physiological parameters at low-cost. The proposed model facilitates low-cost sensor calibration and makes the data quality improvement process more efficient.

Calibration Model Development

Figure 1:
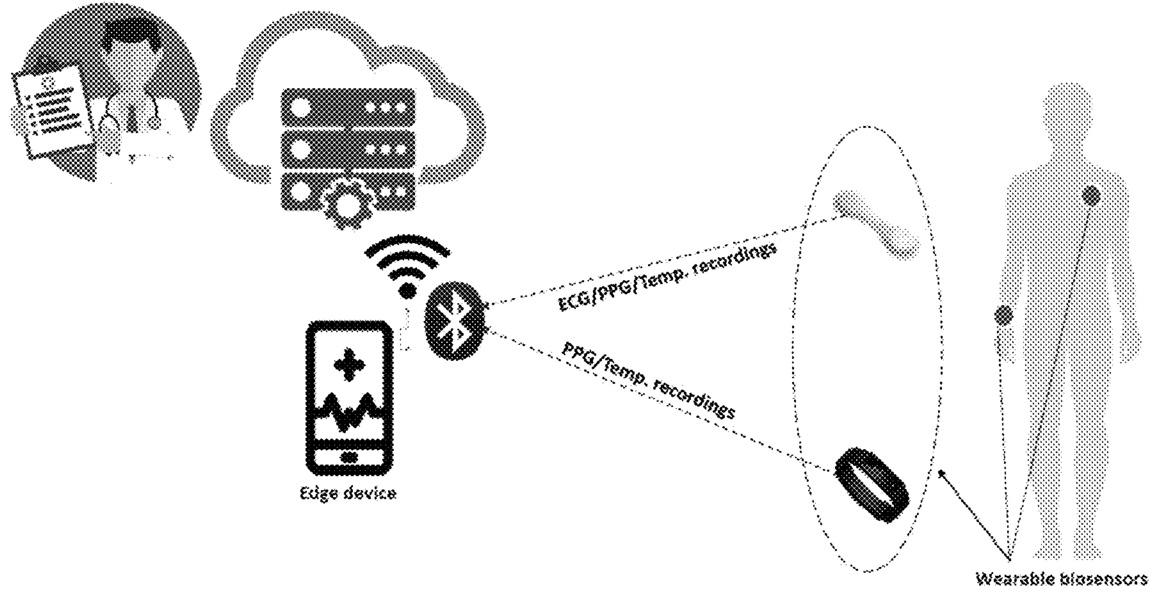
FIG. 1 shows edge computing technology for remote patient monitoring, in which physiological signals (e.g., PPG, ECG, skin temperature) are collected through wearable biosensors (e.g., wristwatch, vital patch) and then sent to an edge device embedded with machine learning algorithms to detect the physiological parameters, which in turn transmits the data flows to a cloud server for analysis.
Figure 2A:
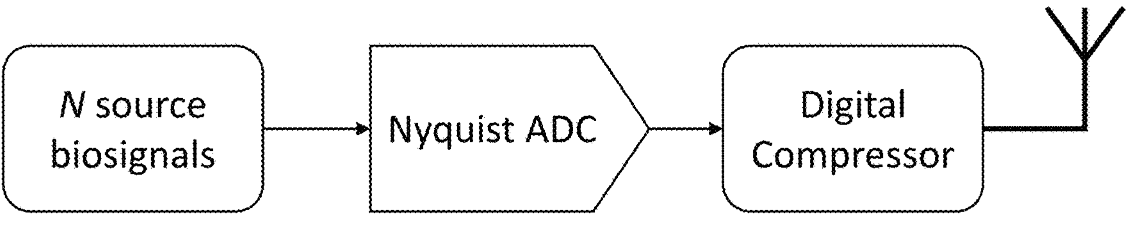
FIGS. 2A and 2B show proposed frameworks for a wearable biosensor and edge device, respectively.
Figure 2B:
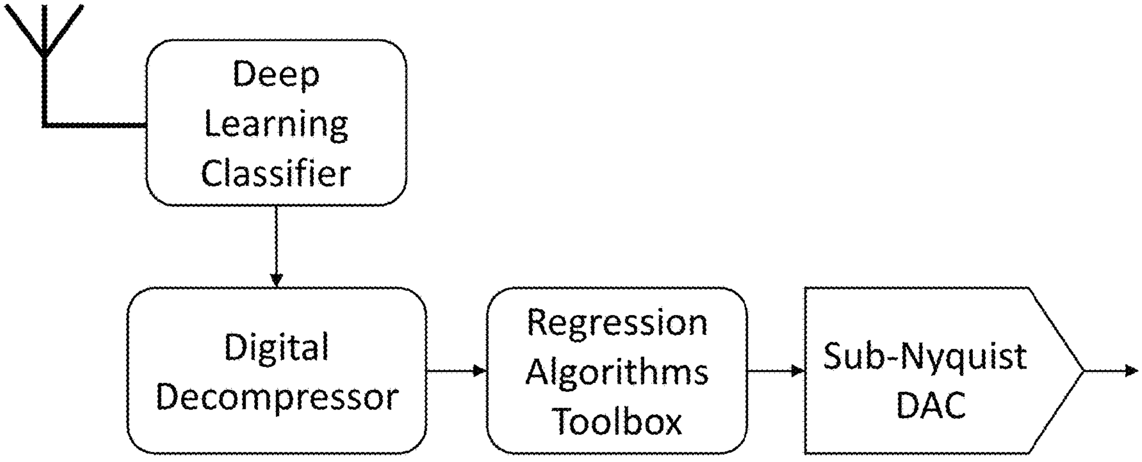

The sensor calibration model consists of two units, a sensing unit that senses the source biosignals (e.g., PPG, ECG, skin temperature, motion) and a data acquisition/detection unit that detects the physiological parameters. In order to develop an energy-efficient sensing framework for remote COVID-19 patient monitoring systems, we implement CS in noisy measurements, where the source biosignals are sparse in the time domain, i.e., the K-source biosignal vector $s_i \in \mathcal{R}^{n\times 1}$ contains K non-zero elements and satisfies $\|s_i\|_{l_0} \leq K << n$, where n is the number of discrete-time samples collected by the i-th biosensor (i=1, . . . , N), which is used to train the DL classifier (e.g., deep neural network). The proposed sensing framework is summarized in the block diagram in FIG. 2.

In the sensing unit, the source biosignals are collected by wearable biosensors (e.g., wristwatch, vital patch) and compressed by a digital CS model [64] to discard the small frequency coefficients of the source biosignals vector $s(t)=[s_1(t), \ldots, s_N(t)]$ due to motion artifacts being measured by a motion sensor (accelerometer), i.e., many frequency coefficients are set to zero after adding a quantization step to the inverse discrete cosine transform vector $\Psi=[\Psi_1, \ldots, \Psi_N]$ (where $\Psi_1 \in \mathcal{R}^{n\times n}$ is a unitary matrix that can discard the small coefficients of $s_i$) to produce a sparse vector, $x(t)=\Psi s(t)$, where we can design the deep neural network to have fewer layers and thus the exploding gradient problem is fixed.

For the data acquisition unit, the edge computing device collects the sparse biosignals vector x(t) for the joint CS-DL recovery, where we assume that the biosignals are corrupted due to RF interference from L external sources (operating in the ISM radio band) with additive white Gaussian noise $n_r \in \mathcal{R}^{m\times n}$, $r \in \{1, \ldots, N+L\}$, where the receiving signal for each biosensor $y_r \in \mathcal{R}^{m\times n}$, at the M-sensor array, is expressed as $$y_r(t) = \sum_{i=1}^{N} h_r x_i^T(t) + \sum_{j=1}^{L} h_r x_j^T(t) + n_r(t), \tag{1}$$

where $h_r \in \mathcal{R}^{m\times 1}$ is a constant channel vector which depend on the distance between the i-th biosensor/the j-th interferer and the edge device, and the $x_j \in \mathcal{R}^{n\times 1}$ is the RF noise artifacts generated by the j-th interferer. The received signal is then processed by the DL classifier $w_r \in \mathcal{R}^{1\times M}$ to extract the signal of interest $\hat{x}_r = w_r y_r$, and remove noise and artifacts as $$\hat{x}_r = \underbrace{w_r h_r x_r^T}_{\text{desired signal}} + \underbrace{\sum_{i \neq r}^{N} w_r h_r x_i^T}_{\text{intra-sensor interference}} + \underbrace{\sum_{j \neq r}^{L} w_r h_r x_j^T}_{\text{inter-sensor interference}} + \underbrace{w_r n_r}_{\text{noise}}, \quad (2)$$

where:

$$w_r = h_r^T.$$

Figure 3:
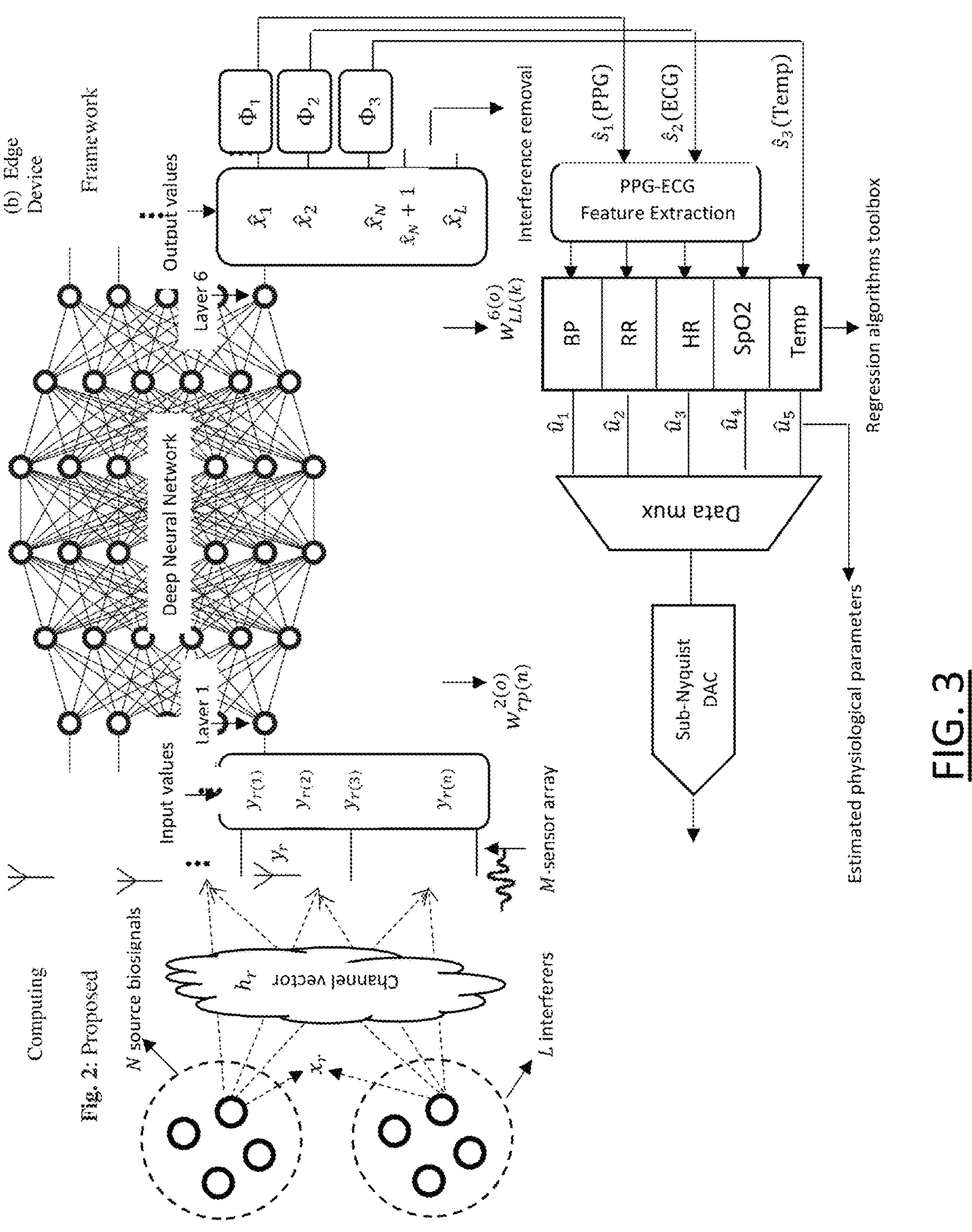
FIG. 3 shows an implementation of a multi-parameter calibration model in inter and intra-sensor interference scenarios where a CS-DL model (embedded into the edge computing device) is used to retrieve source biosignals (e.g., PPG, ECG, skin temperature, motion, where N=4), which can be applied in conjunction with multi-linear regression algorithms to estimate multiple physiological parameters.
Figure 4A:
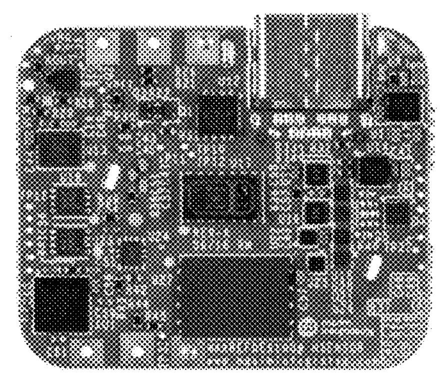
FIGS. 4A and 4B show wearable development platforms, and more specifically MAXREFDES100 (chest-based device) and MAXREFDES101 (wrist-based device), respectively.
Figure 4B:
Figure 5A:
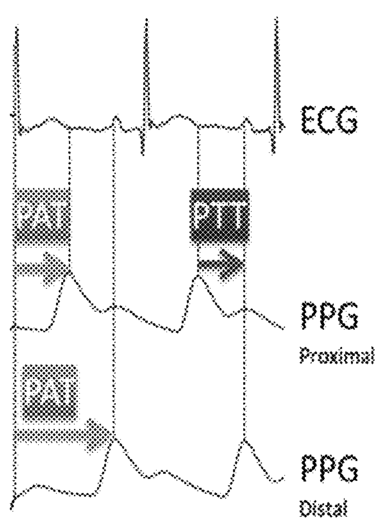
FIGS. 5A through 5C show photoplethysmography-electrocardiogram (PPG-ECG) raw data, and more specifically pulse arrival time/pulse transit time (PAT/PTT) of PPG-ECG, amplitude modulation (AM)/frequency modulation (FM)/baseline wander (BW) of PPG, and Red and IR wavelengths of PPG, respectively.
Figure 5B:
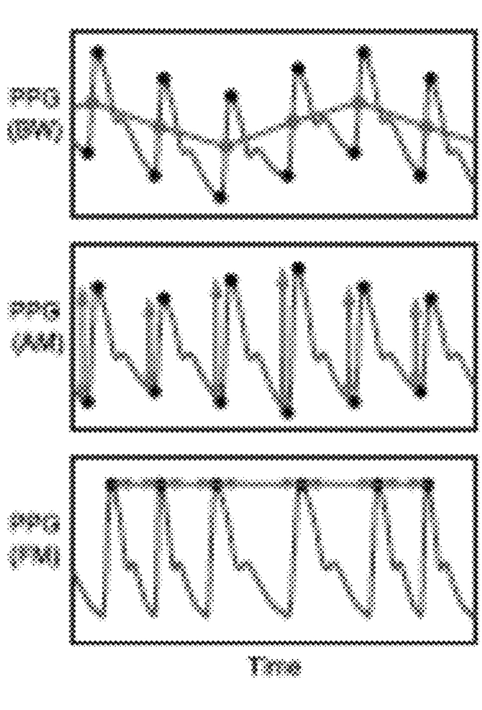
Figure 5C:
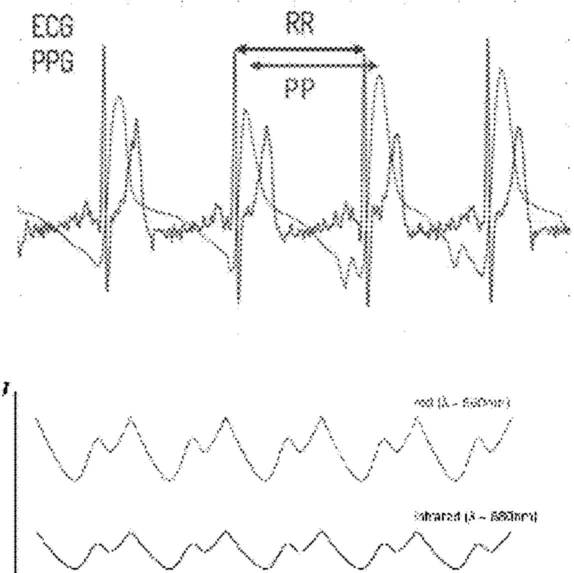

By embedding the pattern recognition problem formulated in (2) into the deep neural network (see FIG. 3), we are building a robust computational model used to detect and classify patterns of biosignals in noisy contexts, where the cost function (mean squared error) is computed as $$C(w_r, b_r) = \frac{1}{n}\sum_{c=1}^{n}(x_{r(c)} - \hat{x}_{r(c)})^2, \quad (3)$$

where the weights $w_r$ and biases $b_r$ are tweaked by applying the gradient descent algorithm and backpropagation [65] over n training samples to minimize the cost function and get the desired output $x_r$, where the activation (e.g., predicted sparse biosignal) $\hat{x}_r$ of the p-th neuron in the l-th layer, is computed as $$\hat{x}_r^{l(o)} = \sigma\left(\sum_k w_{rp(k)}^{l(o)} a_{(k)}^{l-1(o)} + b_{rp}^{l(o)}\right), \quad (4)$$

where: $a^{l-1}$ is the activation of the k-th neuron in the (l−1)-th layer, and o=1, . . . , M is the number of observations. By calculating the average of neural network weights $$w_{rp(k)}^{l(o)}$$

across o observations, we create a more stable model (i.e., better performance in terms of test accuracy) that reduces the cost function. After extracting the sparse biosignals $\hat{x}_r$ (including motion artifacts and interference), we use a digital decompressor where the source biosignal patterns $s_r$ are retrieved with a few measurements m (i.e., low computational time and power consumption to calculate the physiological parameters) using the feasible solution of $\|\hat{s}_r - s_r\|_{l_2} \le C_0\|s_r - s_{r,K}\|_{l_1}/\sqrt{K} + C_1\varepsilon$ to the optimization problem:

$$\min_{s_r}\|s_r\|_{l_1} \text{ s.t. } \min_{s_r}\|A_r s_r - z_r\|_{l_2} \le \varepsilon,$$

where $A_r = \Phi_r \Psi_r$ is the sensing matrix, $\Phi_r \in \mathcal{R}^{m \times n}$ is the measurement matrix n»m»K that obeys the restricted isometry property [6], at which the received signal is given by $z_r = \Phi_r \hat{x}_r$, ε is the maximum noise power, $C_0$ and $C_1$ are constants and are typically small. By capturing high-quality ECG-PPG signals ($s_r$), we can extract the necessary features (e.g., PAT, PTT, PWV, BW, AM, FM, AC/DC PPG components, R-R/P-P intervals, etc.) to estimate the physiological parameters.

To find the relationship between the five predicted physiological parameters $\hat{u}_i$ (dependent variables, l=1, . . . , 5) and features $v_j$ (independent variables, j=1, . . . , V), we apply the selected features to the multiple linear regression algorithm for error modeling and calibration of ECG-PPG sensors, in an attempt to find the best fit or representation of the data points m and make the most accurate predictions, that is, $$\hat{u}_i(t_k) = \beta_0 + \beta_1 v_1(t_k) + \beta_2 v_2(t_k) + \ldots + \beta_V v_V(t_k), \quad (5)$$

where: k=1, . . . , m, $\beta_0$ is the intercept and $\beta_j$ are the regression coefficients (slopes) that are approached by using the gradient descent algorithm. While estimating the BP parameter, the selected V features could be $v_1$ (PTT) and $v_2$ (PWV), where $\hat{u}_{BP}(t_k) = \beta_0 + \beta_1 v_1(t_k) + \beta_2 v_2(t_k)$. To evaluate the performance of the calibration model and measure the strength of the linear relationship, we use the coefficient of determination $R^2$ (the closer $R^2$ is to 1 the better the fit) and root-mean-squared error (RMSE) which tell us how well our regression line matches the real reference data. For instance, RMSE provides a good measure of calibration model error by calculating the distance between predicted values $\hat{u}_k$ and reference values $u_k$, which is defined as $\text{RMSE} = \sqrt{\Sigma_k(\hat{u}_k - u_k)^2/m}$.

Experimental Design

In order to establish a prototype implementation and experimental evaluation of the calibration model, we use various wearable development platforms in the form of wristwatches and vital patches (e.g., MAXREFDES100/101#) that stream raw data from PPG, ECG, skin temperature, and motion sensors on a continuous basis through Bluetooth to android devices (e.g., tablet). Maxim devices and algorithms give FDA-grade PPG-ECG-skin temperature measurement performance, including chest and wrist-based devices. During the experiments, traces of PPG-ECG and other data are collected from all sensors simultaneously to obtain accurate readings of physiological parameters. Vital patches are proven to be more effective in accurate ECG monitoring than wristwatches, especially in fitness applications where the quality of the ECG signal is affected by motion artifacts caused by the wearer's activities. Therefore, in this work, we aim to use different development solutions that overcome the accuracy challenges of wrist-based devices.

Data Collection

Different types of data will be acquired from the large, open-source databases Physionet and GitHub. These contain thousands of physiological signal recordings ("waveforms") and vital signs/physiological parameter time series ("numerics"). Such data includes ECG, PPG, skin temperature, BP, SpO2, HR and RR collected from bedside patient monitors in adult and neonatal ICUs of hospitals. It is also associated with an anonymous clinical dataset containing information on patients who stayed in ICUs between 2010 and 2021. Evidently, this sort of information would be beneficial as a reference to aid with the calibration process and ensure that the biosensors collect accurate data on PPG ($s_1(t)$), ECG ($s_2(t)$), and skin temperature ($s_3(t)$). To detect motion artifacts (anomalies/outliers) in PPG-ECG readings, we use the motion sensors (accelerometers) that are located in the vital patch and wristwatch, where the motion pattern ($s_4(t)$) is used to automatically filter motion artifacts during classification [56], [66-69].

The robustness of the sensor calibration model was tested under a variety of movement conditions during walking, brisk walking, running, and bike riding, in order to detect different patterns of artifact anomalies in PPG-ECG recordings, where we collect an amount of data, e.g., n=15000 data points (samples) which corresponds to 10 minutes of readings acquired at a sampling rate of 25 Hz. In order to reduce the power consumption on the chip and extend the life of the biosensor, we digitally compress the sensor readings through the unitary matrix $\Psi_i \in \mathcal{R}^{n\times n}$, i=1, . . . , N (where N=4), to generate sparse biosignals $x_i(t)=\Psi_i s_i(t)$ where the small coefficients of $s_i(t)$ are discarded with no loss in quality.

RF Interference Modeling

As more and more devices share the scarce radio spectrum as unlicensed ISM bands [5], [59-63], it is important to understand how RF interference affects the performance of wearable biosensors to provide an adequate interference mitigation scheme. To examine the proposed model in RF interference (e.g., inter-sensor interference) surroundings, we assume that the wearable biosensors coexist with various radio technologies operating in the 2.4 GHz ISM frequency band (e.g., Bluetooth, IEEE 802.11b/g/n WiFi, Zigbee) where a received signal strength (RSSI) sampler (e.g., CC2652RB SimpleLink) is used to capture radio emissions from all interferers $x_j(t)$ (where j=1, . . . , L) over different distances, as a series of n reference data values that can be used to detect and classify different interference patterns [70-74]. Since the wearable biosensors use a BLE module (built-in wristwatch/vital patch) to send PPG, ECG, and skin temperature data to the edge device, the impact of RF interference can be diminished unless the non-overlapping channels are occupied by the interferers. BLE uses 40 channels where the adaptive frequency hopping (AFH) algorithm is performed to cycle through 37 data channels to maintain a connection in the presence of interference. For example, if the BLE device operates in the same area of WiFi access points (operating on channels 1, 6, and 11), the BLE device will mark channels: 0-8, 11-20, and 24-32 as noisy channels, where the AFH algorithm cycles through the remaining non-overlapping channels to avoid transmission over noisy channels. The main problem for WiFi/Bluetooth coexistence is that when there are multiple WiFi or Bluetooth piconets in the area of interference, the number of bad channels increases as data packet drops become higher in the interference region [75-78]. However, devices that use frequency hopping, like other BLE devices, can potentially cause the same amount of interference as they normally do. Since all BLE users share the same frequency band, different users' hops may be transmitted at the same frequency at the same time, causing interference between users and deteriorating data quality when the number of users is large [79]. To generate a high mutual interference between Bluetooth, WiFi, and Zigbee wireless technologies, we run the development tool: Bluetooth software development kit (SDK)-v. 2.9 that can update the Bluetooth channel map between the wearable biosensors and the edge device, where the peer BLE devices agree on which channels they will use from the 37 data channels while communicating. We can start the frequency hopping attack by jamming the data channels and leaving a few channels for the BLE device to hop over. During our initial experiments in an unpredictable and uncontrolled interference environment, both the wristwatch and vital patch communicate with the edge device as the Bluetooth/WiFi/Zigbee coexistence test is performed with L interference sources (such as Bluetooth mice, keyboards, and Zigbee/WiFi access points) deployed at Lakehead University, which in turn disrupt the connection between the BLE transceivers and reduce the signal strength of the biosensors.

Physiological Parameters Extraction

Once the corrupted sparse biosignals, biosignals, $y_r(t)$ (for r=1, . . . , N+L), are received by the edge device, the DL classifier is trained with a large dataset size (n×(N+L) samples via o observations, where data flows are visualized by the Android application) that characterizes different types of biosignal patterns and interference, and allows for useful insight into the most powerful features to be selected while calculating the physiological parameters. The main goal of training the classifier is to adapt to various environmental conditions (such as motion artifacts and interference) to detect anomalies in the PPG-ECG readings in order to improve the prediction accuracy of physiological parameters. To train the classifier, we start with random initial guesses of the classifier parameters (i.e., weights $w_r$ and biases $b_r$ between k and p neurons) in the deep neural network. We feed training samples through the network layers (l), and calculate the resulting outputs (e.g., predicted sparse biosignals $\hat{x}_r$) in order to find the class label for biosignals and interference. Then the cost function $C(w_r, b_r)$ in (3) is used to measure the difference between the predicted sparse biosignals and desired outputs $x_r$. By starting at the output layer, we can propagate errors back through the network which allows us to compute the gradient of the cost function with respect to the classifier parameters, i.e., $$\nabla C = \left(\frac{\partial C}{\partial w_{rp(k)}^{l(o)}}, \frac{\partial C}{\partial b_{rp}^{l(o)}}\right)^T.$$

After each iteration across the dataset, the gradient descent algorithm adjusts all the classifier parameters to reduce the cost function, namely, $$w_{rp(k)}^{l(o)} \rightarrow \hat{w}_{rp(k)}^{l(o)} = w_{rp(k)}^{l(o)} - \eta\frac{\partial C}{\partial w_{rp(k)}^{l(o)}},$$

$$b_{rp}^{l(o)} \rightarrow \hat{b}_{rp}^{l(o)} = b_{rp}^{l(o)} - \eta\frac{\partial C}{\partial b_{rp}^{l(o)}},$$

where: η is learning rate. By plugging both weights and biases into the neural network, we can identify the patterns of sparse biosignals, motion artifacts, and interference. By having accurate weights, motion artifacts and inter/intra-sensor interference can be eliminated and sparse PPG-ECG signals retrieved with high quality. To decompress the sparse biosignals, we use the measurement matrix $\Phi_r \in \mathcal{R}^{m\times n}$ to reduce the size of the training dataset and reconstruct the source biosignals, PPG $\hat{s}_1(t)$, ECG $\hat{s}_2(t)$ and skin temperature $\hat{s}_3(t)$, in a few measurements (i.e., less computation time when predicting the physiological parameters). By restoring the source biosignals, the regression algorithms are trained with both the features of the input data extracted from the source biosignals and the output label of the i-th physiological parameter $\hat{u}_i(t_k)$ for k=1, . . . , m.

During calibration, the PPG and ECG sensor measurements are regressed against the reference measurements of physiological parameters, where the multi-linear regression algorithm is applied to fit the biosensor's data to the reference measurement, in which the values of slopes and intercept are calculated using the optimization method (gradient descent) with the aim of finding the best fit or representation of the selected features as described headed 'Calibration Model Development'. The PPG-ECG sensors are first calibrated using all available features (listed in Table I), then a subset of features is selected using the feature selection algorithms (such as forward sequential selection, backward elimination) which try to find a minimum subset of the original features that most contribute to accuracy and discard redundant or noisy features.

To build and train the multi-parameter calibration model (including CS model, DL classifier, and multi-linear regression algorithm), we develop a Python application for use with Android inference toolings [80], such as machine learning Kit-SDK that uses TensorFlow Lite models to efficiently implement machine learning models on mobile devices and other embedded devices that have limited computing and memory resources.

Evaluation Metrics

We evaluate the precision of the calibration model embedded into the edge device to correctly identify clean PPG and ECG readings for the purpose of measuring physiological parameters. Through our data analysis, the main evaluation metrics are the coefficient of determination $R^2$ and RMSE of PPG-ECG readings taken from the wristwatch and vital patch. The performance of calibration model is tested and validated across participants using sensor readings acquired during motion and interference scenarios, where measurement errors on the wristwatch are compared to those obtained by the vital patch.

As described hereinbefore, the present invention relates to a low-cost sensor system that is used to continuously and remotely monitor the five physiological parameters (e.g., skin temperature, oxygen saturation, blood pressure, and heart and respiration rates) of COVID-19 patients. The proliferation of mobile devices and ubiquitous computing has ushered in a new era of the internet of things (IoT). The concept of IoT provides a solid framework for connecting wearables (e.g., wristwatch, vital patch), edge computing devices (e.g., smartphone, tablet) and cloud computing platforms that allow clinicians to monitor the patients' physiological parameters directly and reduce the burden of healthcare costs. Wearable biosensors generate large amounts of patient data that contain motion artifacts and interference that can distort PPG-ECG signals and reduce the detection accuracy of physiological parameters during patient movement. Due to the number of IoT devices operating in the 2.4 GHz-industrial, scientific, and medical (ISM) band increases rapidly, the coexistence problem between wireless networks (such as WiFi, Bluetooth, Zigbee) may also arise, causing radio frequency (RF) interference to edge computing devices, which in turn leads to poor detection accuracy of the physiological parameters. Furthermore, due to continuous patient monitoring, the high-power consumption of Bluetooth low energy (BLE)-enabled devices (such as wearables, edge computing devices) poses another major challenge for researchers to adopt such systems in everyday life. Toward this end, this work develops an accurate multi-parameter calibration model based on edge computing, compressed sensing and machine learning that can be used to address the sensor fault problem due to motion artifacts and noise interference in wearable biosensor networks and can reduce the computational complexity, implementation cost, and energy consumption of wearable and edge devices. The proposed sensing system will have a significant impact on the healthcare sector in Canada and other countries by improving the efficiency, reliability and accuracy of patients' continuous monitoring systems, resulting in better patient diagnosis and treatment options.

The novelty of our invention is the use of a new sensing method that can extract the five physiological parameters (i.e., skin temperature, BP, RR, HR, and SpO2) simultaneously in the presence of motion artifacts and interference. Unlike the traditional sensing methods used in [7-55] that are complex and don't offer a continuous remote BP monitoring feature while walking or exercising, the proposed sensing method employs a multi-parameter calibration model that enables continuous monitoring of the physiological parameters (including BP) of COVID-19 patients, and examines the sensor calibration model when PPG-ECG signals contain motion artifacts and noise interference. The invention idea is to reduce the computational complexity at the sensing units (where wearable PPG-ECG sensors suffer from motion artifacts and interference effects) and compute the five physiological parameters at low-cost through edge computing devices (smartphones). Due to the constant monitoring of patients, the high-power consumption of BLE-enabled devices (e.g., wearables, edge devices) presents another challenge for researchers to adopt such systems in daily use. In order to reduce power consumption and improve the battery life of these devices, we utilize the digital CS-DL models where we can reduce the total amount of data sent by wearables (as the digital CS model is applied to ignore the small frequency coefficients of the sparse PPG-ECG signals due to motion artifacts) and employ low-speed DACs (i.e., sub-Nyquist sampling rates) to restore the sparse biosignals and reduce the power consumption of edge devices, where the DL classifier eliminates motion artifacts and noise in PPG-ECG sensor readings and the CS model reduces the sampling rate and makes the DACs operate at low-speed. Since PPG-ECG signals are very sensitive to artifacts and interference during the continuous measurement procedure, rigorous signal processing is required before the PPG-ECG signals can be used to study the physiological parameters. Earlier efforts have sought to understand how wearable biosensors (i.e., PPG and ECG sensors) identify anomalies/outliers in terms of motion artifacts and how machine learning techniques have adapted to collect and detect multiple labeled datasets of these anomalies [56-58].

Although datasets collected by wearable biosensors, have achieved a reasonable success in detecting and classifying different types of PPG and ECG anomalies, but cannot meet the scale and uninterrupted monitoring that remote patient monitoring agencies require, where there is a continuous movement for the COVID-19 patient, and wearable biosensors interfere with uncontrolled wireless sources (e.g., IoT devices) present in the same building operating in the 2.4 GHz ISM band (e.g., Bluetooth, IEEE 802.11 WiFi, IEEE 802.15.4 (ZigBee), 2.4 GHz RFID/surveillance cameras/microwave ovens) [4], [5]. Indeed, this may increase in the number of COVID-19 patients or ISM users (who can crowd the 2.4 GHz ISM band), leading to poor estimation and detection of the physiological parameters. Therefore, our aim is to design and develop an effective sensor calibration model that uses edge computing, machine learning and compressed sensing to continuously monitor the five physiological parameters at low-cost and eliminate motion artifacts effects caused by patient movement while addressing the coexistence problem of WiFi, Bluetooth, and ZigBee technologies [59-63], which may arise with the further growth of a number of different IoT devices in the 2.4 GHz band, which to the best of our knowledge, has not yet been developed in literature. Specifically, the main contributions of this work can be summarized as follows:

- Developing a low-complexity and cost sensor method that can provide continuous monitoring for the five physiological parameters (e.g., temperature, BP, RR, HR, SpO2) while walking or exercising.
  - Removing motion artifacts from PPG-ECG signals during patient movement and addressing the coexistence problem of WiFi, Bluetooth, and ZigBee technologies (which results in RF interference and lower detection accuracy of the physiological parameters) due to the increase in the number of IoT devices operating in the ISM band.
  - Reducing the power consumption of BLE-enabled devices (e.g., wearables, edge computing devices) while improving data quality and accuracy.
  - Saving time, money, and effort while monitoring the physiological parameters.

Unlike competitors in the e-health market today who don't offer a continuous remote BP monitoring feature while the patient is in motion, our sensor system can monitor the five physiological parameters (including BP) simultaneously in real-time during patient movement. The substantial competitive advantages of the sensor system include:

- Superior software paradigm, complementary to edge computing devices advances in remote medical diagnostics.
- Low-complexity design for BLE-enabled wearable and edge computing devices, i.e., low-cost hardware implementation with low energy consumption.
- High-speed detection of the physiological parameters.
- Continuous monitoring of the physiological parameters with high data accuracy while the patient is in motion.
- Removal of motion artifacts and RF interference from PPG-ECG signals in order to enhance the detection accuracy of physiological parameters.

Figure 6:
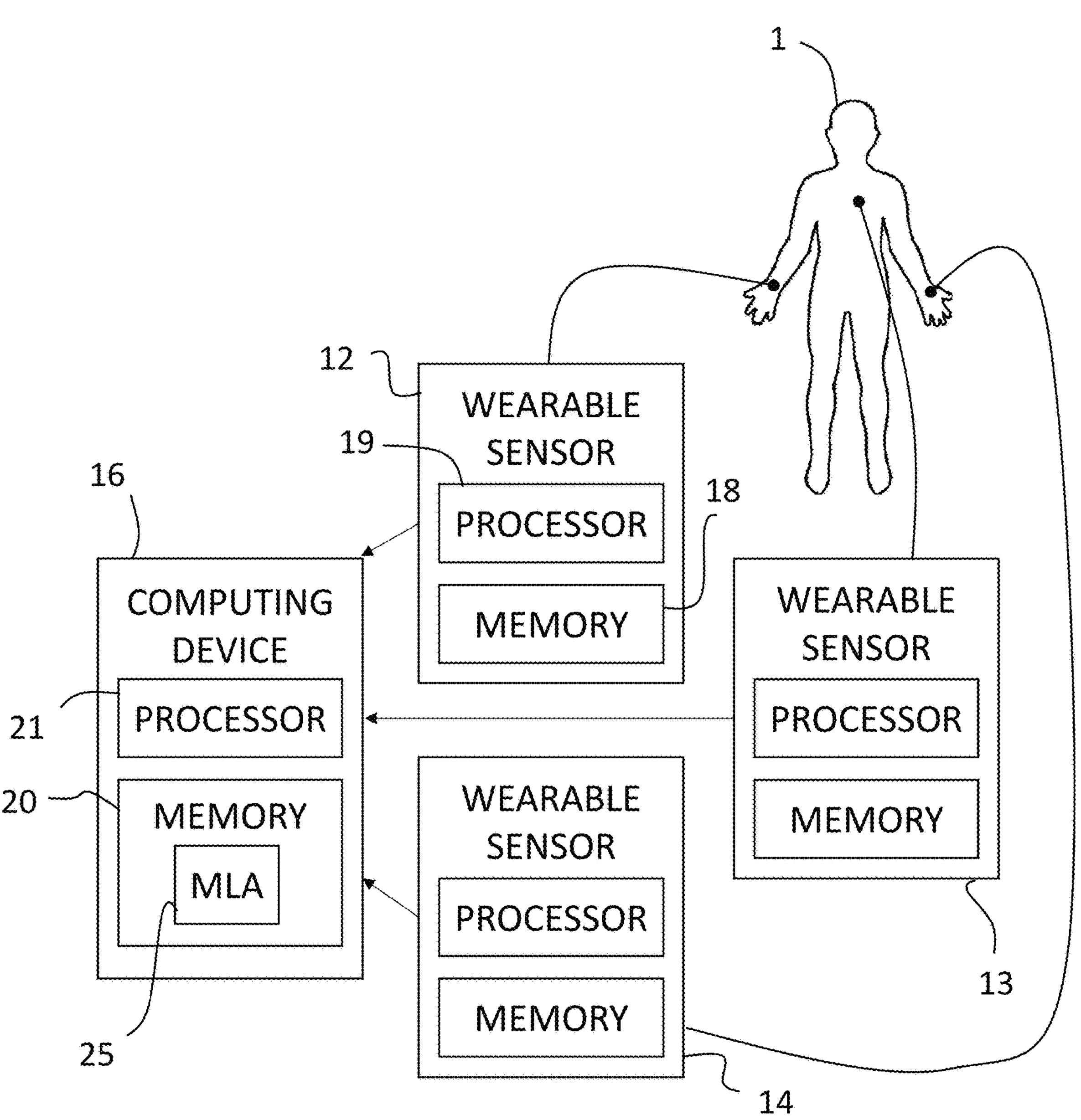
FIG. 6 is a schematic diagram of a system for monitoring a physiological parameter of a subject according to an arrangement of the present invention.

FIG. 6 shows a system 10 for monitoring a physiological parameter of a monitored subject 1, which comprises (i) at least one wearable sensor such as 12, 13 or 14 configured for attaching to the monitored subject 1, so as to be worn thereby, and configured to measure a biosignal, from which the physiological parameter is deducible, so as to form a measured signal including data representative of the physiological parameter and noise data; and (ii) a portable computing device 16 operatively communicated with the wearable sensor 12, 13 or 14 to receive a transmitted signal therefrom, in this case by wireless communication.

Each wearable sensor 12, 13 or 14 comprises a non-transitory memory 18 and a processor 19 operatively connected thereto and configured to execute instructions stored on the non-transitory memory 18 to substantially remove, from the measured signal, the noise data so as to form a cleaned signal. Furthermore, the portable computing device 16 comprises a non-transitory memory 20 and a processor 21 operatively connected thereto and configured to execute instructions stored on the non-transitory memory 20 of the portable computing device to determine the physiological parameter from the transmitted signal.

As such, the signal received by the portable computing device for further processing to deduce the physiological parameter, referred to as the transmitted signal, comprises both measurement noise, that is noise imparted on the captured biosignal during a measurement operation performed by the respective sensor such as motion or movement of the sensor, and transmission noise, that is noise imparted on the signal during communication from the sensor to the computing device. Transmission noise may include electromagnetic interference from other electronic devices which emit electromagnetic fields that are either part of the system or otherwise accounted for thereby, and environmental or ambient noise from other electromagnetic fields present in an operating environment of the system.

To determine the physiological parameter from the transmitted signal, in the illustrated arrangement the instructions stored on the non-transitory memory 20 of the portable computing device 16 to determine the physiological parameter from the transmitted signal comprise a machine learning algorithm (MLA) 25. To assist with the foregoing, the machine learning algorithm 25 is configured to substantially remove from the transmitted signal noise data associated with electromagnetic interference to isolate the cleaned signal therefrom.

Also, the machine learning algorithm 25 is configured to substantially remove from the transmitted signal noise data associated with motion of the wearable sensor to isolate the cleaned signal therefrom. Motion data of the subject is captured by a wearable sensor configured for attaching to the monitored subject and configured to measure motion of the monitored subject to form motion data to train the machine learning algorithm for removing the noise data associated with motion of the wearable sensor. This can be one of the sensors 12-14 measuring a biosignal or a distinct sensor that is additionally configured therefor.

Figure 7:
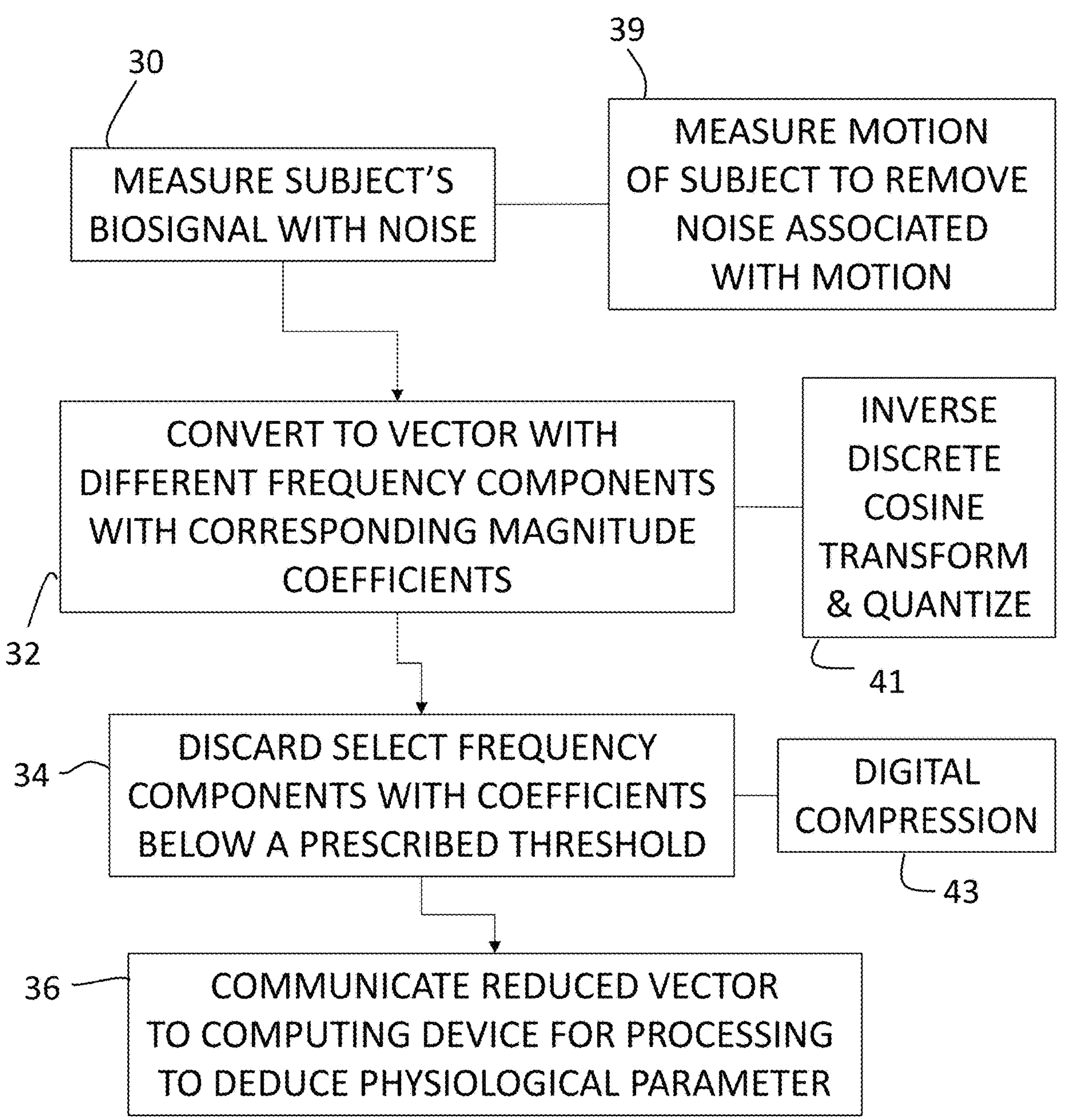
FIG. 7 is a flowchart of a method of collecting data on a physiological parameter of a subject according to an arrangement of the present invention.

With reference to FIG. 7, to distribute processing burden for removing noise data to determine the physiological parameter from the biosignal, each sensor 12, 13 or 14 is configured to perform the following steps as a method of collecting data on the physiological parameter of the subject:

i) measuring a biosignal, from which the physiological parameter is deducible, to form a signal comprising data representative of the physiological parameter and noise data, as represented at step 30;
ii) converting the signal to a vector having a plurality of different frequency components each with a corresponding magnitude coefficient, as indicated at step 32;
iii) discarding from the vector select ones of the frequency components with coefficients below a prescribed threshold to form a reduced vector, as indicated at step 34; and
iv) as at 36, communicating the reduced vector to a computing device, that is the device indicated at 16, for processing to deduce the physiological parameter.

In the illustrated arrangement, measuring the biosignal comprises measuring at least one of body temperature, heartbeat, and blood flow. When there are multiple sensors, such as those indicated at 12 through 14, each measures a different biosignal of the monitored subject from which the common physiological parameter is deducible. This may improve accuracy of the calculated or determined physiological parameter.

In the illustrated arrangement, since the step of measuring the biosignal at 30 is performed using a wearable sensor such as 12, the noise data comprises noise associated with movement of the wearable sensor. Movement of the sensor primarily stems from movement of the subject to whom the sensor is generally fixedly attached and who is free to move around when wearing wearable sensors that are wirelessly communicated with the processing unit in the form of a portable computing device such as a smartphone. As such, preferably, the prescribed threshold for discarding frequency components is based on noise associated with movement of a wearable sensor.

In the illustrated arrangement, the data collection method further includes measuring motion of the monitored subject to form motion data usable to remove the noise data from the measured biosignal, as indicated at 39. This is performed concurrently with measuring the biosignal.

In the illustrated arrangement, converting the signal to a vector comprises performing an inverse discrete cosine transform on the signal and quantizing the transformed signal, as indicated at 41.

Figure 8:
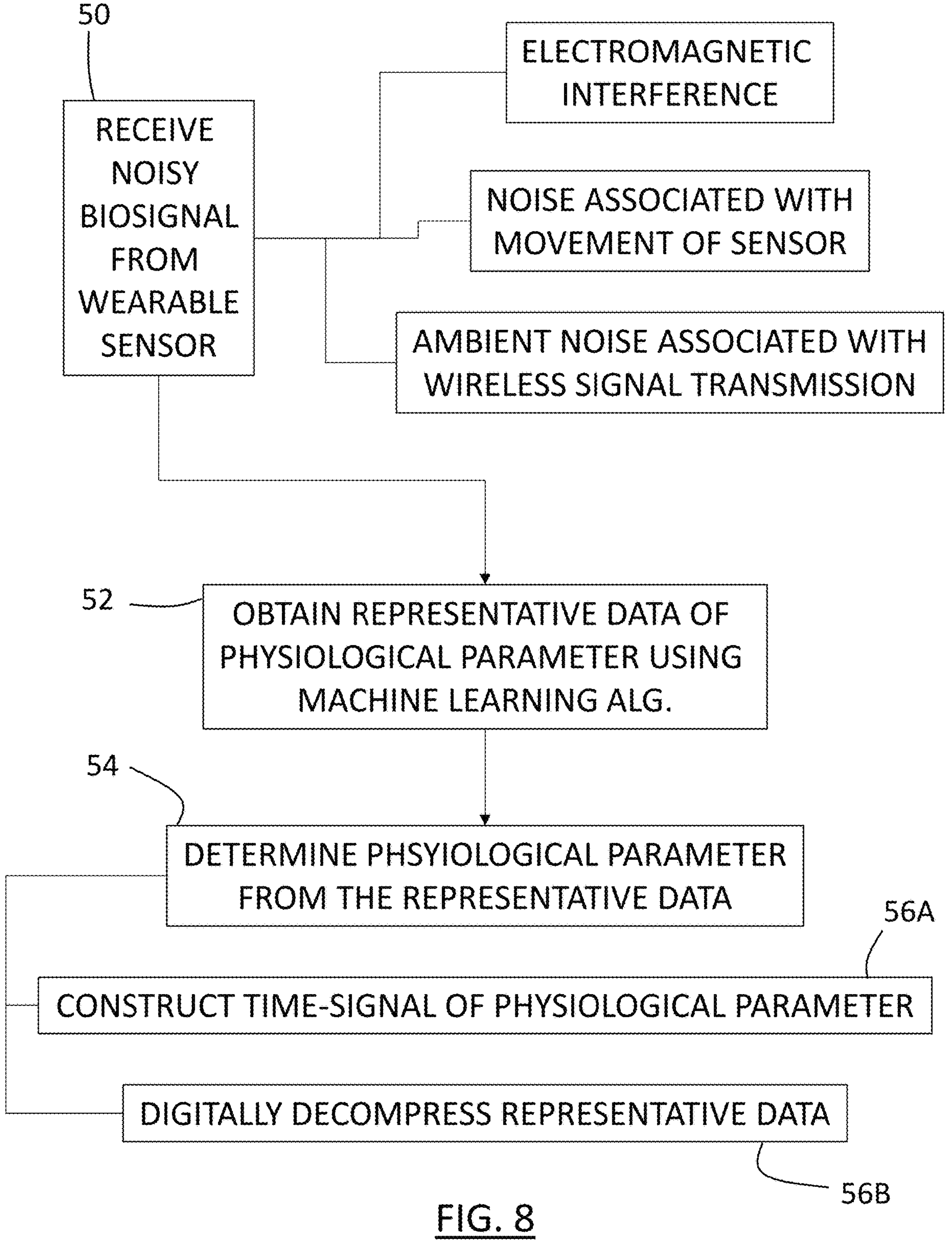
FIG. 8 is a flowchart of a method of processing data collected on a physiological parameter of a subject according to an arrangement of the present invention.

In the illustrated arrangement, discarding select frequency components from the vector to form the reduced vector comprises digitally compressing the vector. With reference to FIG. 8, the computing device 16 is configured to perform the following steps as a method of processing data collected on the physiological parameter of the subject:

a) as indicated at 50, receiving a noisy signal of a measured biosignal, which includes data representative of the physiological parameter and noise data;

b) as indicated at 52, obtaining from the noisy signal the data representative of the physiological parameter using a machine learning algorithm 25; and c) as indicated at 54, determining the physiological parameter from the data representative of thereof, which is obtained by the machine learning algorithm.

It will be appreciated that the noise data comprises noise associated with electromagnetic interference.

The machine learning algorithm 25 comprises an artificial neural network and a pattern recognition learning model.

The pattern recognition learning model comprises a cost function configured to adjust weights and biases of the artificial neural network using gradient descent and back-propagation. Furthermore, the pattern recognition learning model comprises an activation function configured to average weights of the artificial neural network over a plurality of observations. Moreover, the pattern recognition learning model is configured to determine a relationship between the physiological parameter and features extracted by the machine learning algorithm from the noisy signal using multiple linear regression.

Since in the illustrated arrangement the noisy signal is received from a plurality of wearable wireless sensors 12-14, the noise data additionally comprises overlapping data from the sensors, noise associated with movement of the wearable sensors and ambient noise, and the machine learning algorithm is configured to substantially remove this noise data.

In the illustrated arrangement, the step of determining the physiological parameter from the data representative thereof, which is obtained by the machine learning algorithm, and indicated at 54, comprises constructing a time-signal of the physiological parameter based on this data as indicated at 56A.

Furthermore, constructing the time-signal comprises digitally decompressing the data representative of the physiological parameter obtained using the machine learning algorithm 25.

The scope of the claims should not be limited by the preferred embodiments set forth in the examples but should be given the broadest interpretation consistent with the specification as a whole.

REFERENCES

[1] H. U. Chung et al., "Binodal, wireless epidermal electronic systems with in-sensor analytics for neonatal intensive care," *Science*, vol. 363, no. 6430, pp. 947, March 2019.

[2] C. El-Hajj and P. A. Kyriacou, "A review of machine learning techniques in photoplethysmography for the non-invasive cuff-less measurement of blood pressure", *Biomed. Signal Process. Control,* 58, 101870, 2020.

[3] J. Lee et al., "Motion Artifact Reduction in Wearable Photoplethysmography Based on Multi-Channel Sensors with Multiple Wavelengths". *Sensors,* 20, 1493, 2020.

[4] D. Cypher, N. Chevrollier, N. Montavont, and N. Golmie, "Prevailing over wires in healthcare environments: benefits and challenges," *IEEE Commun. Mag.*, vol. 44, no. 4, pp. 56-63, 2006.

[5] A. Hithnawi, "*Low-power Wireless Systems Coexistence*," Thesis, Doctor of Science, ETH Zurich, 2016.

[6] Y. C. Eldar "*Sampling Theory: Beyond Bandlimited Systems*," Cambridge University Press, April 2015.

[7] M. Kachuee, M. M. Kiani, H. Mohammadzade, and M. Shabany, "Cuffless blood pressure estimation algorithms for continuous health-care monitoring," *IEEE Trans. Biomed. Eng.*, vol. 64, no. 4, pp. 859-869, 2017.

[8] H. Mamaghanian et al. Compressed Sensing for Real-Time Energy Efficient ECG Compression on Wireless Body Sensor Nodes. *IEEE Trans. Biomed. Eng,* 58(9): 2456-2466, September 2011.

[9] M. S. Tanveer and M. K. Hasan, 'Cuffless blood pressure estimation from electrocardiogram and photoplethysmogram using waveform-based ANN-LSTM network', *Biomed. Signal Process. Control*, vol. 51, pp. 382-392, 2019.

[10] V. R. Ripoll and A. Vellido, "Blood pressure assessment with differential pulse transit time and deep learning: a proof of concept", Kidney Dis., pp. 23-27, 2019.

[11] R. Lazazzera, Y. Belhaj, and G. Carrault, "A new wearable device for blood pressure estimation using photoplethysmogram," *Sensors*, vol. 19, no. 11, p. 2557, 2019.

[12] M. Elgendi, R. Fletcher, Y. Liang, N. Howard, N. H. Lovell, D. Abbott, K. Lim, and R. Ward, "The use of photoplethysmography for assessing hypertension," *NPJ Digit. Med.*, vol. 2, no. 1, p. 60, December 2019.

[13] M. A. F. Pimentel, P. H. Charlton, and D. A. Clifton, "Probabilistic estimation of respiratory rate from wearable sensors," in *Wearable Electronics Sensors*, vol. 15, S. C. Mukhopadhyay, Ed. New York, NY, USA: Springer, pp. 241-262, 2015.

[14] P. H. Charlton et al., "Extraction of respiratory signals from the electrocardiogram and photoplethysmogram: Technical and physiological determinants," *Physiol. Meas.*, vol. 38, no. 5, pp. 669-690, 2017.

[15] M. A. Motin, C. K. Karmakar, and M. Palaniswami, "Ensemble empirical mode decomposition with principal component analysis: A novel approach for extracting respiratory rate and heart rate from photoplethysmographic signal," *IEEE J. Biomed. Health Inform.*, vol. 22, no. 3, pp. 766-774, May 2018.

[16] P. H. Charlton, D. A. Birrenkott, T. Bonnici, M. A. F. Pimentel, A. E. W. Johnson, J. Alastruey, L. Tarassenko, P. J. Watkinson, R. Beale, D. A. Clifton, "Breathing rate estimation from the electrocardiogram and photoplethysmogram: a review", *IEEE Reviews in Biomedical Engineering,* 99, 1-17, 2017.

[17] H. Liu, J. Allen, D. Zheng, and F. Chen, "Recent development of respiratory rate measurement technologies," *Physiol. Meas.*, vol. 40, no. 7, p. 07TR01, August 2019.

[18] P. H. Charlton et al., "An assessment of algorithms to estimate respiratory rate from the electrocardiogram and photoplethysmogram," *Physiological Measurement*, 2016.

[19] V. Ravichandran, B. Murugesan, V. Balakarthikeyan, S. M. Shankaranarayana, K. Ram, J. Joseph, M. Sivaprakasam et al., "Respnet: A deep learning model for extraction of respiration from photoplethysmogram," arXiv preprint arXiv:1902.04236, 2019.

[20] C. Phillips, D. Liaqat, M. Gabel, and E. Lara,. "Wrist02—Reliable Peripheral Oxygen Saturation Readings from Wrist-Worn Pulse Oximeters". arXiv: 1906.07545 [cs, eess], June 2019.

[21] T. Vandenberk, J. *Stans*, C. Mortelmans et al, "Clinical validation of heart rate apps: mixed-methods evaluation study". *JMIR Mhealth Uhealth*, 5(8), e129, 2017.

[22] D. Biswas, N. Simues-Capela, C. Van Hoof, and N. Van Helleputte, "Heart rate estimation from wrist-worn photoplethysmography: A review," *IEEE Sensors Journal*, 2019.

[23] A. Kiruthiga, A. Annamol, T. Balamugesh, R. D. Prabhu, D. Christopher, S. Preejith, J. Jayaraj, and S. Mohanasankar, "Reflectance pulse oximetry for blood oxygen saturation measurement from diverse locations-a preliminary analysis," in 2018 *IEEE International Symposium on Medical Measurements and Applications* (MeMeA), pp. 1-6, 2018.

[24] Maxim Integrated Products, Inc, "*Application Note* 6845 Guidelines for SpO2 Measurement using the MAXIM® MAX32664 Sensor Hub, 2019. [Online]: www.maximintegrated.com/en/design/technical-documents/app-notes/6/6845.html

[25] Michael Sawh, "ECG smartwatches: How they work and the best on the market", February 2021. [Online]: www.wareable.com/health-and-wellbeing/ecg-heart-rate-monitor-watch-guide-6508

[26] Dave Muoio, "Samsung says smartwatch ECG, blood pressure measurement will go live in 31 more countries", January 2021. [Online]: www.mobihealthnews.com

[27] J. Jain, J. Young, C. Wortham, S. Sadi, and P. Mistry. "Improving performance of biological measurements in the presence of noise." PCT Patent WO2017217599, issued Jul. 2020.

[28] D. Mccombie, M. Dhillon, and M. Banet. "Method for generating alarms/alerts based on a patient's posture and vital signs." U.S. Patent 20100298661, issued Feb. 2020.

[29] J. Moon, H. Visser, and R. Hunt. "Body-worn vital sign monitor" U.S. Pat. No. 10,806,351, issued Oct. 2020.

[30] J. Jain, J. Young, C. Wortham, S. Sadi, and P. Mistry. "Continuous stress measurement with built-in alarm fatigue reduction features." PCT Patent WO2017217600, filed September 2016.

[31] B. H. CHOI, H. w. KOHH, Y. S. Kim, H. J. BAEK, J. W. Shin, C. Y. Yoon, and J. G Cho. "Apparatus for measuring blood pressure, and method for measuring blood pressure by using same." U.S. Patent 20180353089, filed Nov. 2016.

[32] Y. Gross and D. H. Lange. "Monitoring health status of people suffering from chronic diseases." EU Patent 3307146, issued Nov. 2020.

[33] B. Tran. "Personal monitoring system." US Patent 20140143064, issued May. 2015.

[34] M. Murphy, R. Norman, M. Christopher, and T. Lengerich. "Method for Improving Heart Rate Estimates by Combining Multiple Measurement Modalities." US Patent 20210015379, filed September 2020.

[35] Z. Zhang, "Photoplethysmography-Based Heart Rate Monitoring in Physical Activities via Joint Sparse Spectrum Reconstruction," *IEEE Trans Biomed Eng*, v.62, pp. 1902-1910, 2015.

[36] V. P. Rachim, and W. Y. Chung. "Compressive Sensing of Cuff-less Biosensor for Energy-Efficient Blood Pressure Monitoring." 2019 41$^{st}$ *Annual International Conference of the IEEE Engineering in Medicine and Biology Society* (*EMBC*), 2019.

[37] V. Natarajan, A. Vyas, Power efficient compressive sensing for continuous monitoring of ECG and PPG in a wearable system, in: 2016 *IEEE 3rd World Forum on Internet of Things*, WF-IoT 2016, pp. 336-341, 2017.

[38] M. Hooshmand, D. Zordan, D. Del Testa, E. Grisan, and M. Rossi, "Boosting the battery life of wearables for health monitoring through the compression of biosignals," *IEEE Internet Things J*., vol. 4, no. 5, pp. 1647-1662, October 2017.

[39] V. Dang, T. Phan and O. Kilic, "Compressive sensing-based approach for detection of human respiratory rate," 2015 *IEEE International Symposium on Antennas and Propagation & USNC/URSI National Radio Science Meeting*, Vancouver, BC, pp. 394-395, 2015.

[40] P. K. Baheti, "An ultra low power pulse oximeter sensor based on compressed sensing," Proc. *Wearable and Implantable Body Sensor Networks*, pp. 144-148, 2009.

[41] Y. Alghorani and S. Ikki, "An Information-Theoretic Framework for Joint CS-ICA Recovery of Sparse Biosignals," techrxiv preprint, September 2020, https://doi.org/10.36227/techrxiv.12923891.v2

[42] D. Mccombie, M. Dhillon, M. Banet, G. Trommer, and J. Moon. "Body-worn system for continuously monitoring a patients BP, HR, SpO2, RR, temperature, and motion; also describes specific monitors for apnea, ASY, VTAC, VFIB, and 'bed sore' index." U.S. Pat. No. 8,956,294, issued Feb. 2015.

[43] M. Banet, M. S. Dhillon, S. M. Pede, L. N. M. Hayward, A. Deptala, and J. D. Cochran. "Combined floormat and body-worn physiological sensors." U.S. Pat. No. 9,757,042, issued September 2017.

[44] K. U. K. Menon, S. Krishna, K. V. Edayillam, G. Bindu, H. Krishnannair, and M. V. Ramesh. "Spectroscopic monitoring for the measurement of multiple physiological parameters." U.S. patent Ser. No. 16/232,288, filed Jun. 2019.

[45] M. Banet, M. Dhillon, and D. Mccombie. "Body-worn system for measuring continuous non-invasive blood pressure (cNIBP)." U.S. Pat. No. 10,765,326, issued September 2020.

[46] S. Eletr, G. S. Golda, M. P. Marriott, B. O'Neil, G. E. Smith, D. V. Zandt Moyer. "Health monitoring systems and methods." U.S. patent Ser. No. 15/844,116, issued Apr. 2020.

[47] S. F. LeBoeuf, J. B. Tucker, M. E. Aumer, E. D. Romesburg, and J. N. Morris. "Apparatus and methods for monitoring physiological data during environmental interference." U.S. Pat. No. 8,888,701, issued Nov. 2014.

[48] V. Mouradian. "Non-invasive wearable respiration rate monitoring system." U.S. Pat. No. 10,117,598, issued Nov. 2018.

[49] V. Mouradian, and A. Poghosyan. "Non-invasive wearable blood pressure monitoring system." U.S. Pat. No. 10,327,649, issued Jun. 2019.

[50] S. F. LeBoeuf, M. E. Aumer, and E. D. Romesburg. "Method and apparatus for generating assessments using physical activity and biometric parameters." U.S. Pat. No. 10,413,250, issued September 2019.

[51] M. E. Aumer, and S. F. LeBoeuf. "Physiological monitoring devices and methods that identify subject activity type." U.S. Pat. No. 10,610,158, issued Apr. 2020.
[52] S. Soro, R. F. Donehoo, and 0. V. Pekander. "Wireless patient monitoring system and method." U.S. Pat. No. 9,814,388, issued Nov. 2017.
[53] A. R. Connor. "Wearable computing devices and methods for the wrist and/or forearm." U.S. Pat. No. 9,582,035, issued Feb. 2017.
[54] W. Chung, and A. Kaveh. "Method and apparatus for wireless health monitoring and emergent condition prediction." U.S. Pat. No. 10,055,549, issued Aug. 2018.
[55] M. Fahey. "Remote health monitoring system." U.S. Pat. No. 10,332,379, issued Jun. 2019.
[56] P. C.-P. Chao et al. "A portable, wireless photoplethysomography sensor for assessing health of arteriovenous Fistula using class-weighted support vector machine," *Sensors* (*Basel*), 18, 2018.
[57] Q. Zhang, X. Zeng, W. Hu, and D. Zhou, "A machine learning empowered system for long-term motion-tolerant wearable monitoring of blood pressure and heart rate with ear-ECG/PPG," *IEEE Access*, vol. 5, pp. 10547-10561, 2017.
[58] D. Pollreisz and N. Taherinejad, "Detection and removal of motion artifacts in PPG signals," *Mobile Networks and Applications*, August 2019.
[59] H. Karvonen, K. Mikhaylov, D. Acharya, and M. M. Rahman, "Performance Evaluation of Bluetooth Low Energy Technology under Interference," *In Proceedings of the 13th EAI International Conference on Body Area Networks*, Oulu, Finland, 2-3 Oct. 2018.
[60] H. Hellbruck and T. Esemann, "Limitations of frequency hopping in 2.4 GHz ISM-Band for medical applications due to interference," in *Proc. IEEE Consum. Commun. Netw. Conf.*, pp. 242-246, January 2011.
[61] H. Karvonen, K. Mikhaylov, M. Hamalainen, J. Iinatti, and C. PomalazaRaez, "Interference of wireless technologies on BLE based WBANs in hospital scenarios," in *IEEE International Symposium on Personal Indoor and Mobile Radio Communications* (*PIMRC*), 2017.
[62] R. Challoo, A. Oladeinde, N. Yilmazer, S. Ozcelik, and L. Challoo, "An Overview and Assessment of Wireless Technologies and Coexistence of ZigBee, Bluetooth and Wi-Fi Devices," *Procedia Computer Science*, vol. 12, pp.386-391, 2012.
[63] HP Technical White Paper "Protecting medical devices and reducing patient risk from electromagnetic interference", 4AA7-6297ENW, November 2020. [Online]: www8.hp.com/h20195/v2/GetDocumentaspx?docname=4AA7-6297ENW
[64] F. Chen, A. P. Chandrakasan, and V. Stojanovic, "Design and analysis of a hardware-efficient compressed sensing architecture for data compression in wireless sensors," *IEEE J. Solid-State Circuits*, vol. 47, pp. 744-756, March 2012.
[65] M. A. Nielsen, "*Neural networks and deep learning*," Determination Press, vol. 1, 2014.
[66] D. Yang et al., "A novel adaptive spectrum noise cancellation approach for enhancing heartbeat rate monitoring in a wearable device," *IEEE Access*, vol. 6, pp. 8364-8375, 2018.
[67] P. Fonseca, R. M. Aarts, X. Long, J. Rolink and S. Leonhardt, "Estimating actigraphy from motion artifacts in ECG and respiratory effort signals," *Physiol. Meas.*, vol. 37, pp. 67-82, 2016.
[68] M. Wang, Z. Li, Q. Zhang, and G. Wang, "Removal of motion artifacts in photoplethysmograph sensors during intensive exercise for accurate heart rate calculation based on frequency estimation and notch filtering," *Sensors* (*Switzerland*), vol. 19, no. 15, p. 3312, July 2019.
[69] Y. Zhang, et al., "Motion Artifact Reduction for Wrist-Worn Photoplethysmograph Sensors Based on Different Wavelengths" *Sensors*, vol. 19, no. 3, p.673, 2019.
[70] G. Shi, K. Li. "Interference Avoidance in ZigBee Networks. In: Signal Interference in WiFi and ZigBee Networks. Wireless Networks". Springer, Cham. 2017.
[71] M. Alawami and H. Kim, "LocAuth: A fine-grained indoor location-based authentication system using wireless networks characteristics". *Computers & Security,* 89, p.101683, 2020.
[72] F. Sadikin, and K. Sandeep. "ZigBee IoT Intrusion Detection System: A Hybrid Approach with Rule-based and Machine Learning Anomaly Detection." In *IoTBDS*, pp. 57-68. 2020.
[73] M. del Horno, M., I. Garcia-Varea, and L. Orozco Barbosa. "Calibration of Wi-Fi-based indoor tracking systems for Android-based smartphones." *Remote Sensing* 11, no. 9, 2019.
[74] G. Zhang, P. Wang, H. Chen, and L. Zhang, "Wireless Indoor Localization Using Convolutional Neural Network and Gaussian Process Regression," *Sensors*., vol. 19, no. 11. 2508, 2019.
[75] A. B. Kasem, A. S. Binte Awal and M. R. Hasan, "Interference mitigation in coexisting bluetooth and WLAN network using power efficiency method," 2012 *International Conference on Computer, Information and Telecommunication Systems* (*CITS*), Amman, pp. 1-5, 2012.
[76] A. Nikoukar, S. Raza, A. Poole, M. Güneş, and B. Dezfouli, "Low-power wireless for the Internet of Things: Standards and applications," *IEEE Access, vol.* 6, pp. 67893-67926, 2018.
[77] F. Hermans et al., "SoNIC: Classifying interference in 802.15.4 sensor networks," in *Proc. ACM/IEEE Int. Conf. Inf. Process. Sensor Netw.* (*IPSN*), Philadelphia, PA, USA, pp. 55-66, April 2013.
[78] 0. A. Bamandi and S. A. Zummo, "An adaptive frequency hopping techniquewith application to Bluetooth-WLAN coexistence," in *Proc. Int. Conf. Netw., Int. Conf. Syst. Int. Conf. Mobile Commun. Learn. Technol.* (*ICNICONSMCL*), p. 131. 2006.
[79] Y. Ren, Z. Ni, L. Kuang, S. Wu, and J. Lu, "Joint interference estimation and cancellation for coherent frequency hopping multiple access systems," *EURASIP Journal on Wireless Communications and Networking*, vol. 2016, no. 1, p. 182, August 2016.
[80] Developer.android.com/ml Tables

TABLE I

Extraction of PPG-ECG features in order to estimate physiological parameter.

| Physiological parameter | Features |
|---|---|
| BP | PTT, PAT, PWV, ST, DT, HR [7-12] |
| RR | AM, BW, FM [13-19] |
| HR | R-R/P-P intervals [3], [20-22] |
| SpO2 | AC/DC PPG components at red and IR wavelengths [20], [23], [24] |

The invention claimed is:

1. A method of overcoming signal noise in measurement and wireless transmission of electrocardiogram (ECG) and photoplethysmography (PPG) biosignals of actively mobile subjects using non-invasive wearables for transmission to mobile devices over low power wireless communication to enable real-time evaluation and continuous monitoring of multiple physiological parameters of said actively mobile subjects, the method comprising:

(a) by non-invasive ECG and PPG sensors embodied among one or more wearable devices worn by an actively mobile patient:

(i) measuring a ECG and PPG biosignals of the mobile patient and performing real-time conversion thereof into digital ECG and PPG signals, in which there is embodied noise that is of detrimental relation to accurate measurement of the physiological parameters and includes both motion artifacts and electromagnetic interference;

(ii) converting said noisy digital ECG and PPG signals into digitally compressed ECG and PPG signals by performing, in real-time, inverse discrete cosine transformation of said noisy digital ECG and PPG signals and quantization of the transformed noisy digital ECG and PPG signals to derive vector representations thereof composed of frequency components and associated coefficients, and discarding a subset of said frequency components whose associated coefficients fall below a threshold such that the digitally compressed ECG and PPG signals comprise sparse vector data representative of both the ECG and PPG biosignals and said noise, and transmitting, via a low power wireless communication protocol, said digitally compressed noisy signals from the one or more wearable devices;

(b) in concurrent relation to step (a), and by one or more motion sensors embodied among said one or more wearable devices worn by the actively mobile patient, capturing motion data representative of body motion of the actively mobile patient during capture of the measured ECG and PPG biosignals and transmitting, via a low power wireless communication protocol, said motion data from the one or more wearable devices;

(c) by a mobile edge-computing device borne by the actively mobile patient, receiving, via said low power wireless communication protocol, of both the digitally compressed ECG and PPG signals and the motion data from the one or more wearable devices;

(d) by said mobile edge-computing device of the actively mobile subject, and through execution thereby of a machine learning algorithm trained to detect and classify patterns between sparse ECG and PPG signals and noise factors including at least said motion artifacts and said electromagnetic interference, using the digitally compressed ECG and PPG signals and the motion data from the one or more wearable devices as combined input to the machine learning algorithm to calculate, in real-time, estimated noiseless sparse vector ECG and PPG signals from which said motion artifacts are filtered out during classification using said motion data;

(e) by said mobile edge-computing device, decompressing said estimated noiseless sparse ECG and PPG signals, in real-time, to reconstruct source ECG and PPG biosignals therefrom;

(f) by said mobile edge-computing device, applying a multi-linear regression algorithm to features extracted from the reconstructed source ECG and PPG biosignals to calculate, in real-time, estimated noiseless quantifications of the physiological parameter;

(g) outputting, in real time and by said mobile edge-computing device, said estimated noiseless quantifications of the physiological parameters; and (h) continuously repeating steps (a) through (g) for continuous real-time monitoring of the physiological parameters;

wherein the multiple physiological parameters comprise at least a plurality of skin temperature, oxygen saturation, blood pressure, heart rate and respiration rate, and the machine learning algorithm comprises a classifier trained using random initial guesses of weights and biases of neurons in a deep neural network, through which training samples were fed through layers thereof to calculate predicted sparse vector ECG-PPG signals to find a class label for ECG-PPG signals and noise interference, and a cost function used to measure difference between the predicted sparse vector ECG-PPG signals and desired outputs, with application of gradient descent and backpropagation over multiple training samples to minimize the cost function through adjustment of the weights and biases, arriving at weights that configure the classifier to eliminate the motion artifacts, and accurately derive the estimated noiseless sparse vector ECG and PPG signals, in step (d).

2. The method of claim 1 wherein the one or more biosensors comprise a plurality of biosensors, and the noise data and the noise factors further comprise data overlap from the plurality of sensors.

3. The method of claim 1 wherein, when the compressed noisy signal is wirelessly received from the one or more biosensors, and the noise data and the noise factors further comprise ambient noise.

4. The method of claim 1 wherein the multiple physiological parameters comprise at least three of said skin temperature, oxygen saturation, blood pressure, heart rate and respiration rate.

5. The method of claim 1 wherein the multiple physiological parameters comprise at least four of said skin temperature, oxygen saturation, blood pressure, heart rate and respiration rate.

6. The method of claim 1 wherein the multiple physiological parameters comprise all five of said skin temperature, oxygen saturation, blood pressure, heart rate and respiration rate.

7. The method of claim 1 wherein the one or more wearable devices comprise a smartwatch.

8. The method of claim 1 wherein the one or more wearable devices comprise a smart patch.

9. The method of claim 1 wherein the one or more wearable devices comprise a smartwatch and a smart patch.

10. The method of claim 1 wherein said low power wireless communication protocol is Bluetooth Low Energy (BLE).

11. The method of claim 1 wherein said mobile edge computing device is a smartphone.

12. The method of claim 1 wherein the one or more wearable devices comprise at least one of a smartwatch and a smart patch, and said mobile edge computing device comprises a smartphone.

13. The method of claim 12 wherein said low power wireless communication protocol is Bluetooth Low Energy (BLE).

14. The method of claim 1 further comprising wireless transmission of the estimated physiological parameters by and from the mobile edge computing device to a remote patient-monitoring entity.

15. The method of claim 1 further comprising monitoring said estimated noiseless quantifications of the physiological parameters for changes therein over time, and alerting the actively mobile patient upon detection of changes indicative of a health concern.

16. The method of claim 14 further comprising monitoring said estimated noiseless quantifications of the physiological parameters for changes therein over time, and alerting the actively mobile patient upon detection of changes indicative of a health concern.

17. The method of claim 14 further comprising monitoring, by said remote patient-monitoring entity, of said estimated noiseless quantifications of the physiological parameters for changes therein over time, and alerting the actively mobile patient upon detection of changes indicative of a health concern.

18. The method of claim 15 wherein said health concern is a transmissible virus.

19. The method of claim 16 wherein said health concern is a transmissible virus.

20. The method of claim 17 wherein said health concern is a transmissible virus.

* * * * *